(12) United States Patent
Yu et al.

(10) Patent No.: US 8,394,619 B1
(45) Date of Patent: Mar. 12, 2013

(54) BETA-GLUCOSIDASE AND USES THEREOF

(75) Inventors: Su-May Yu, Taipei (TW); Tuan-Hua David Ho, Chesterfield, MO (US); Hsion-Wen Kuo, Chiayi (TW); Ng I-Son Wu, Yung-Kang (TW); Chen-Wei Li, Changhua County (TW); Yu-Ming Ju, Shi-Jr (TW)

(73) Assignee: Academia Sinica, Taipei (TW)

( * ) Notice: Subject to any disclaimer, the term of this patent is extended or adjusted under 35 U.S.C. 154(b) by 2657 days.

(21) Appl. No.: 13/575,457

(22) PCT Filed: Jan. 28, 2011

(86) PCT No.: PCT/US2011/022906
§ 371 (c)(1),
(2), (4) Date: Nov. 8, 2012

(87) PCT Pub. No.: WO2011/094530
PCT Pub. Date: Aug. 4, 2011

Related U.S. Application Data

(60) Provisional application No. 61/299,007, filed on Jan. 28, 2010.

(51) Int. Cl.
*C07K 1/00* (2006.01)
*C07H 21/02* (2006.01)
*C12N 9/38* (2006.01)
*C12N 1/20* (2006.01)
*C12N 15/00* (2006.01)

(52) U.S. Cl. .......... 435/207; 435/252.3; 435/320.1; 530/350

(58) Field of Classification Search .......... 435/183, 435/252.3, 320.1
See application file for complete search history.

(56) References Cited

PUBLICATIONS

NCBI GenBank accession No. XP_001591221 Hypothetical protein SS1G_07847 [*Sclerotinia sclerotiorum* 1980 UF-70] Feb. 26, 2008.
NCBI GenBank accession No. XP_001547429 'Hypothetical protein BC1G_14164 [*Botryotinia fuckeliana* B05.10]' Feb. 26, 2008.
Gangadevi, V. and Muthumary, J. 'A novel endophytic taxol-producing fungus *Chaetomella raphigera* isolated from a medicinal plant, *Terminalia arjuna*' Applied Biochemistry and Biotechnology. vol. 158(3), pp. 675-684 (Feb. 21, 2009).
NG, I. S. et al, 'Dynamic synergistic effect on *Trichoderma reesei* cellulases by novel beta-glucosidases from Taiwanese fungi' Bioresource Technology. vol. 102(10), pp. 6073-6081 (Jan. 12, 2011).

*Primary Examiner* — Maryam Monshipouri
(74) *Attorney, Agent, or Firm* — Occhiuti Rohlicek & Tsao LLP

(57) ABSTRACT

A novel beta-glucosidase and nucleic acids encoding the beta-glucosidase. Also disclosed are cells, compositions, and methods relating to using the beta-glucosidase to convert ligocellulosic material to fermentable sugars.

21 Claims, 9 Drawing Sheets

```
 -34                    ATG AAA TCT CGA GCC TTC ACT TTC GCA GCC CTA GCT GTA CCA AGC CTA GCT GCT  -1
 -10                     M   K   S   R   A   F   T   F   A   A   L   A   V   P   S   L   A   A   -1
   1 CCT GGT GAT GGT GAT TGG GCA GCG GCT TAT AAA AAA GCT ACC GCT GCT CTC GCA AAA TTG AGC AAC ACC GAC AAA    75
   1  P   G   D   G   D   W   A   A   A   Y   K   K   A   T   A   A   L   A   K   L   S   N   T   D   K   25
     GCC AGT ATT GTT ACT GGC GTG GGT TGG GAA AAG GGT CCT TGC GTT GGG AAT ACT GCT GCA GTA GCA TCA ATT GGA   150
      A   S   I   V   T   G   V   G   W   E   K   G   P   C   V   G   N   T   A   A   V   A   S   I   G   50
     CTT CCA GAG CTT TGC TAT CAA GAT GGA CCC CTA GGC ATC CGT TTC GTC CAA AAT GTA ACA GCA TTT CCT ACA GGT   225
      L   P   E   L   C   Y   Q   D   G   P   L   G   I   R   F   V   Q   N   V   T   A   F   P   T   G   75
     ATT CAG ACT GCT TCC ACG TGG GAC ATT AGT TTG ATC TAC AGT CGA GGT TTA GCT TTA GGT CAG GAG GCA AAG GCA   300
      I   Q   T   A   S   T   W   D   I   S   L   I   Y   S   R   G   L   A   L   G   Q   E   A   K   A  100
     CTT GCC ATC AAT GTC CAC CTC GGT CCA GTT GCT GGT CCC ATT CGT AAA ATT CCA GAG GCC GGT CCC AAC TGG GAA   375
      L   G   I   N   V   H   L   G   P   V   A   G   P   I   G   K   I   P   E   A   G   R   N   W   E  125
     GGC TTT TCT CCA GAT CCA TAC CTG AAT GGT CTA GCA ATG TCC AAT ACC ATT ACC GGA ATG CAA GAT GCT GGC GTA   450
      G   F   S   P   D   P   Y   L   N   G   L   A   M   S   N   T   I   T   G   M   Q   D   A   G   V  150
     CAG GCT TGT GCA AAG CAC TTT ATT GGA AAC GAG CAA GAA ACG AAT CGC GAT ACA ATG AGC TCC AAC ATC GAT GAT   525
      Q   A   C   A   K   H   F   I   G   N   E   Q   E   T   N   R   D   T   M   S   S   N   I   D   D  175
     CGG ACT TTC CAT GAG TTG TAC CTC TGG CCT TTC GCA GAT GCC ATC AAG GCC AAC GTT GCA TCC ATA ATG TGC TCA   600
      R   T   F   H   E   L   Y   L   W   P   F   A   D   A   I   K   A   N   V   A   S   I   M   C   S  200
     TAC AAC AAG TTC AAT GAG ACA TAC GCT TGT GAG AAC AAC TTC TTG ACA ACT ATT CTC AAG GGC GAG CTT GAC TTT   675
      Y   N   K   F   N   E   T   Y   A   C   E   N   N   F   L   T   T   I   L   K   G   E   L   D   F  225
     CAA GGC TTC GTC GTC AGC GAC TGG GCT GCT CAG CAT ACT ACT ATT GGA AGT GCA AAT GCT GGT CTG GAT GTT GCG   750
      Q   G   F   V   V   S   D   W   A   A   Q   H   T   T   I   G   S   A   N   A   G   L   D   V   A  250
     ATG CCT GGT GAC AAT TTT GGC GAC AAC TAT TAT CTA TGG GGC AGC AAT CTT CTG GCG GCG ATC TCC AAC GGC ACT   825
      M   P   G   D   N   F   G   D   N   Y   Y   L   W   G   S   N   L   L   A   A   I   S   N   G   T  275
     GTT GCC CAA TCT CGC CTT GAT GAC ATG GTC ACT CGC ATC CTG GCT TCA TGG TAC TTT GTT GGT CAG GAC CAA GGC   900
      V   A   Q   S   R   L   D   D   M   V   T   R   I   L   A   S   W   Y   F   V   G   Q   D   Q   G  300
     TAT CCA CCT GTC ACC TGC TCC TCT TGG AAT GGT GGA TTG GGA GGT CCG AAT GTT CAG GCT GAT CAT AAG CAG GTC   975
      Y   P   A   V   T   W   S   S   W   N   G   G   L   G   G   P   N   V   Q   A   D   H   K   Q   V  325
     GCA CGC GCC ATC GCC CGA GAT GGC ATT GTC CTA CTC ACG AAC AAA AAC AAA GCC CTG CCC CTG AAG AAG CCC GCT  1050
      A   R   A   I   A   R   D   G   I   V   L   L   T   N   K   N   K   A   L   P   L   K   K   P   A  350
     AGT TTA GCA ATC ATT GGT CAA GAT GCC ATC GAC AAT CCT GCA GGC ATC AAC TGC TCC GAC CGC GGT TGT GAT  1125
      S   L   A   I   I   G   Q   D   A   I   D   N   P   A   G   I   N   C   S   D   R   G   C   D  375
     ACG GGT CAC TTG GCT ATG GGT TGG GGC TCG GGC ACA GCA GAC TTT CCA TAC CTC GTT GCG CCG CTC GAT GCC ATC  1200
      T   G   H   L   A   M   G   W   G   S   G   T   A   D   F   P   Y   L   V   A   P   L   D   A   I  400
     ACA CCC TTA GCT CAG GCC CAG GGA ACA AAG CTT GTA TTG TCG ACG ACC GAC AGT ACT TCT GCC GCT GCT AGT GCT  1275
      T   P   L   A   Q   A   Q   G   T   K   L   V   L   S   T   T   D   S   T   S   A   A   A   S   A  425
     GCC GCC GCC GCA GAG ACA GCA ATC GTC TTC ATC ACT GCC GAT TCA GGA GAG GGA TAC ATC ACT GTT GAC GGC CAA  1350
      A   A   A   E   T   A   I   V   F   I   T   A   D   S   G   E   G   Y   I   T   V   D   G   Q  450
     TTG GGT GAT CGC AAC TCA CTT GCT CCA TGG AAT AAT GGC ACT GCT CTC GTT CAA GCG GTA GCC AGC GCC AGC AAA  1425
      L   G   D   R   N   S   L   A   P   W   N   N   G   T   A   L   V   Q   A   V   A   S   A   S   K  475
     AAT GTC ATT GTC GTG ATC AAC AGT GTC GGC CCA TTG ATT CTC GAG GAC ATT CTC GCT CTT TCC AGC GTG AAA GCA  1500
      N   V   I   V   V   I   N   S   V   G   P   L   I   L   E   D   I   L   A   L   S   S   V   K   A  500
     ATT GTC TGG GCT GGC GTC TCG GGC CAA GAA TCG GGC AAT GGA CTT GCT GAT ATT CTT TAC GGT TCA GTA TCT CCC  1575
      I   V   W   A   G   V   S   G   Q   E   S   G   N   G   L   A   D   I   L   Y   G   S   V   S   P  525
     AGT GGG AAA CTC CCA TAC ACA ATC GCC AAA CAG GCC AGC GAC TAT GGA ACA GCC ATT GTG CCC GGT GAC GAT AAC  1650
      S   G   K   L   P   Y   T   I   A   K   Q   A   S   D   Y   G   T   A   I   V   P   G   D   D   N  550
     TTT CCC GAA GGA TTG TTT GTA GAC TAT CGT CAT TTC GAC CAA GCA AAC ATC CAG CCG CGT TTT GAA TTT GGC TAT  1725
      F   P   E   G   L   F   V   D   Y   R   H   F   D   Q   A   N   I   Q   P   R   F   E   F   G   Y  575
     GGC CTC TCC TAT ACG ACC TTT CAA TAC TCG CAG CTT ACC GCA AAG TAC TCC GAT ACT TCC GCA GGC AGC TCC ACT  1800
      G   L   S   Y   T   T   F   Q   Y   S   Q   L   T   A   K   Y   S   D   T   S   A   G   S   S   T  600
     CTC GCC CCT GGC GGA CCC AAG GGG CTG TAT GAT ATT GTT GCA ACG GTA ACA AAG GTG ACA AAC AGC GGC ACC  1875
      L   A   P   G   G   P   K   G   L   Y   D   I   V   A   T   V   T   K   V   T   N   S   G   T  625
     GTC AGT GGC GCT GAA GTC CCA CAG CTA TAC ATT GGT TTG CCC CGC TCG GCG CCT GCA TCT CCA CCC AAC CAG CTA  1950
      V   S   G   A   E   V   P   Q   L   Y   I   G   L   P   G   S   A   P   A   S   P   P   K   Q   L  650
     CGC GGC TTT GAC AAA ATC AGC CTC AAG CCA GGC AAA TCA GGC ACG GTG ACG TTT AAC CTG CGC CGA AAG GAC CTC  2025
      R   G   F   D   K   I   S   L   K   P   G   K   S   G   T   V   T   F   N   L   R   R   K   D   L  675
     AGC TAC TGG GAT ACT GCC TCG GCT CAG TGG GTT ACA CCG ACC AGC GGC GAG TTC TCC CTG TAT GTT GGT GCT AGC  2100
      S   Y   W   D   T   A   S   A   Q   W   V   T   P   T   S   G   E   F   S   L   Y   V   G   A   S  700
     TCG AGA GAT ATA AGG TTA CAG GGG TCT TTG AAA TGC TCG GGC CAA GGT ATT CGG AAA GGT GGA CAT             2166
      S   R   D   I   R   L   Q   G   S   L   K   C   S   G   Q   G   I   R   K   G   G   H             722
```

Fig. 2

SEQUENCE LISTING

<160> NUMBER OF SEQ ID NOS: 18

<210> SEQ ID NO 1
<211> LENGTH: 722
<212> TYPE: PRT
<213> ORGANISM: Chaetomella raphigera

<400> SEQUENCE: 1

```
Pro Gly Asp Gly Asp Trp Ala Ala Tyr Lys Lys Ala Thr Ala Ala
1               5                   10                  15

Leu Ala Lys Leu Ser Asn Thr Asp Lys Ala Ser Ile Val Thr Gly Val
            20                  25                  30

Gly Trp Glu Lys Gly Pro Cys Val Gly Asn Thr Ala Ala Val Ala Ser
            35                  40                  45

Ile Gly Leu Pro Glu Leu Cys Tyr Gln Asp Gly Pro Leu Gly Ile Arg
        50                  55                  60

Phe Val Gln Asn Val Thr Ala Phe Pro Thr Gly Ile Gln Thr Ala Ser
65                  70                  75                  80

Thr Trp Asp Ile Ser Leu Ile Tyr Ser Arg Gly Leu Ala Leu Gly Gln
                85                  90                  95

Glu Ala Lys Ala Leu Gly Ile Asn Val Gln Leu Gly Pro Val Ala Gly
            100                 105                 110

Pro Ile Gly Lys Ile Pro Glu Ala Gly Arg Asn Trp Glu Gly Phe Ser
        115                 120                 125

Pro Asp Pro Tyr Leu Asn Gly Leu Ala Met Ser Asn Thr Ile Thr Gly
    130                 135                 140

Met Gln Asp Ala Gly Val Gln Ala Cys Ala Lys His Phe Ile Gly Asn
145                 150                 155                 160

Glu Gln Glu Thr Asn Arg Asp Thr Met Ser Ser Asn Ile Asp Asp Arg
                165                 170                 175

Thr Phe His Glu Leu Tyr Leu Trp Pro Phe Ala Asp Ala Ile Lys Ala
            180                 185                 190

Asn Val Ala Ser Ile Met Cys Ser Tyr Asn Lys Phe Asn Glu Thr Tyr
        195                 200                 205

Ala Cys Glu Asn Asn Phe Leu Thr Thr Ile Leu Lys Gly Glu Leu Asp
    210                 215                 220

Phe Gln Gly Phe Val Val Ser Asp Trp Ala Ala Gln His Thr Thr Ile
225                 230                 235                 240

Gly Ser Ala Asn Ala Gly Leu Asp Val Ala Met Pro Gly Asp Asn Phe
                245                 250                 255

Gly Asp Asn Tyr Tyr Leu Trp Gly Ser Asn Leu Leu Ala Ala Ile Ser
            260                 265                 270
```

```
Asn Gly Thr Val Ala Gln Ser Arg Leu Asp Asp Met Val Thr Arg Ile
        275                 280                 285

Leu Ala Ser Trp Tyr Phe Val Gly Gln Asp Gln Gly Tyr Pro Ala Val
        290                 295                 300

Thr Trp Ser Ser Trp Asn Gly Leu Gly Gly Pro Asn Val Gln Ala
305                 310                 315                 320

Asp His Lys Gln Val Ala Arg Ala Ile Ala Arg Asp Gly Ile Val Leu
                325                 330                 335

Leu Thr Asn Lys Asn Lys Ala Leu Pro Leu Lys Lys Pro Ala Ser Leu
                340                 345                 350

Ala Ile Ile Gly Gln Asp Ala Ile Asp Asn Pro Ala Gly Ile Asn Ser
            355                 360                 365

Cys Ser Asp Arg Gly Cys Asp Thr Gly His Leu Ala Met Gly Trp Gly
    370                 375                 380

Ser Gly Thr Ala Asp Phe Pro Tyr Leu Val Ala Pro Leu Asp Ala Ile
385                 390                 395                 400

Thr Pro Leu Ala Gln Ala Gln Gly Thr Lys Leu Val Leu Ser Thr Thr
                405                 410                 415

Asp Ser Thr Ser Ala Ala Ser Ala Ala Ala Ala Glu Thr Ala
                420                 425                 430

Ile Val Phe Ile Thr Ala Asp Ser Gly Glu Gly Tyr Ile Thr Val Asp
            435                 440                 445

Gly Gln Leu Gly Asp Arg Asn Ser Leu Ala Pro Trp Asn Asn Gly Thr
    450                 455                 460

Ala Leu Val Gln Ala Val Ala Ser Ala Ser Lys Asn Val Ile Val Val
465                 470                 475                 480

Ile Asn Ser Val Gly Pro Leu Ile Leu Glu Asp Ile Leu Ala Leu Ser
                485                 490                 495

Ser Val Lys Ala Ile Val Trp Ala Gly Val Ser Gly Gln Glu Ser Gly
                500                 505                 510

Asn Gly Leu Ala Asp Ile Leu Tyr Gly Ser Val Ser Pro Ser Gly Lys
            515                 520                 525

Leu Pro Tyr Thr Ile Ala Lys Gln Ala Ser Asp Tyr Gly Thr Ala Ile
    530                 535                 540

Val Pro Gly Asp Asp Asn Phe Pro Glu Gly Leu Phe Val Asp Tyr Arg
545                 550                 555                 560

His Phe Asp Gln Ala Asn Ile Gln Pro Arg Phe Glu Phe Gly Tyr Gly
                565                 570                 575

Leu Ser Tyr Thr Thr Phe Gln Tyr Ser Gln Leu Thr Ala Lys Tyr Ser
            580                 585                 590

Asp Thr Ser Ala Gly Ser Ser Thr Leu Ala Pro Gly Gly Pro Lys Gly
    595                 600                 605

Leu Tyr Asp Ile Val Ala Thr Val Thr Ala Lys Val Thr Asn Ser Gly
    610                 615                 620

Thr Val Ser Gly Ala Glu Val Ala Gln Leu Tyr Ile Gly Leu Pro Gly
625                 630                 635                 640

Ser Ala Pro Ala Ser Pro Pro Lys Gln Leu Arg Gly Phe Asp Lys Ile
                645                 650                 655

Ser Leu Lys Pro Gly Lys Ser Gly Thr Val Thr Phe Asn Leu Arg Arg
            660                 665                 670

Lys Asp Leu Ser Tyr Trp Asp Thr Ala Ser Ala Gln Trp Val Thr Pro
    675                 680                 685

Thr Ser Gly Glu Phe Ser Leu Tyr Val Gly Ala Ser Ser Arg Asp Ile
690                 695                 700
```

Arg Leu Gln Gly Ser Leu Lys Cys Ser Gly Gln Gly Ile Arg Lys Gly
705                 710                 715                 720

Gly His

<210> SEQ ID NO 2
<211> LENGTH: 2166
<212> TYPE: DNA
<213> ORGANISM: Chaetomella raphigera

<400> SEQUENCE: 2

```
cctggtgatg gtgattgggc agcggcttat aaaaaagcta ccgctgctct cgcaaaattg      60
agcaacaccg acaaagccag tattgttact ggcgtgggtt gggaaaaggg tccttgcgtt     120
gggaatactg ctgcagtagc atcaattgga cttccagagc tttgctatca agatggaccc     180
ctaggcatcc gtttcgtcca aaatgtaaca gcatttccta caggtattca gactgcttcc     240
acgtgggaca ttagtttgat ctacagtcga ggtttagctt taggtcagga ggcaaaggca     300
cttggcatca atgtccagct cggtccagtt gctggtccca ttggtaaaat tccagaggcc     360
ggtcgcaact gggaaggctt ttctccagat ccataccctga atggtctagc aatgtccaat     420
accattaccg aatgcaaga tgctggcgta caggcttgtg caaagcactt tattggaaac      480
gagcaagaaa cgaatcgcga tacaatgagc tccaacatcg atgatcggac tttccatgag     540
ttgtacctct ggcctttcgc agatgccatc aaggccaacg ttgcatccat aatgtgctca     600
tacaacaagt tcaatgagac atacgcttgt gagaacaact tcttgacaac tattctcaag     660
ggcgagcttg actttcaagg cttcgtcgtc agcgactggg ctgctcagca tactactatt     720
ggaagtgcaa atgctggtct ggatgttgcg atgcctggtg acaattttgg cgacaactat     780
tatctatggg gcagcaatct tctggcggcg atctccaacg gcactgttgc ccaatctcgc     840
cttgatgaca tggtcactcg catcctggct tcatggtact tgttggtca ggaccaaggc     900
tatccagctg tgacctggtc tcttggaat ggtggattgg gaggtcccaa tgtgcaggct     960
gatcataagc aggtcgcacg cgccatcgcc cgagatggca ttgtcctact cacgaacaaa    1020
aacaaagccc tgcccctgaa gaagcccgct agtttagcaa tcattggtca agatgccatc    1080
gacaatcctg caggcatcaa ctcgtgctcc gaccgcggtt gtgatacggg tcacttggct    1140
atgggttggg gctcgggcac agcagacttt ccatacctcg ttgcgccgct cgatgccatc    1200
acacccttag ctcaggccca gggaacaaag cttgtattgt cgacgaccga cagtacttct    1260
gccgctgcta gtgctgccgc cgccgcagag acagcaatcg tcttcatcac tgccgattca    1320
ggagagggat acatcactgt tgacggccaa ttgggtgatc gcaactcact tgctccatgg    1380
aataatggca ctgctctcgt tcaagcgta gccagcgcca gcaaaaatgt cattgtcgtg    1440
atcaacagtg tcggcccatt gattctcgag acattctcg ctctttccag cgtgaaagca    1500
attgtctggg ctggcgtctc gggccaagaa tcggcaatg gacttgctga tattctttac    1560
ggttcagtat ctcccagtgg gaaactccca tacacaatcg ccaaacaggc cagcgactat    1620
ggaacagcca ttgtgcccgg tgacgataac tttcccgaag gattgtttgt agactatcgt    1680
catttcgacc aagcaaacat ccagccgcgt tttgaatttg gctatggcct ctcctatacg    1740
acctttcaat actcgcagct taccgcaaag tactccgata cttccgcagg cagctccact    1800
ctcgcccctg gcggacccaa ggggctgtat gatattgttg caacggtaac agcaaaggtg    1860
acaaacagcg gcaccgtcag tggcgctgaa gtcgcacagc tatacattgg tttgccgggc    1920
tcggcgcctg catctccacc caagcagcta cgcggctttg acaaaatcag cctcaagcca    1980
```

```
ggcaaatcag gcacggtgac gtttaacctg cgccgaaagg acctcagcta ctgggatact    2040
gcctcggctc agtgggttac accgaccagc ggcgagttct ccctgtatgt tggtgctagc    2100
tcgagagata taaggttaca ggggtctttg aaatgctcgg gccaaggtat tcggaaaggt    2160
ggacat                                                              2166

<210> SEQ ID NO 3
<211> LENGTH: 2851
<212> TYPE: DNA
<213> ORGANISM: Chaetomella raphigera

<400> SEQUENCE: 3
cctggtgatg gtgattgggc agcggcttat aaaaaagcta ccgctgctct cgcaaaattg     60
agcaacaccg acaaagccag tattgttact ggcgtgggtt gggaaaaggg tccttgcgtt    120
gggaatactg ctgcagtagc atcaattgga cttccagagc tttgctatca agatggaccc    180
ctagggtagg ctgctggtta tttgtagtct cagaactgac ggtgaaagca tccgtttcgt    240
ccaaaatgta acagcatttc ctacaggtat tcagactgct tccacgtggg acattagttt    300
gatctacagt cgaggtttag ctttaggtaa gtccaagtac gctgtcaaga tttgaattaa    360
gagtattagg tcaggaggca aaggcacttg gcatcaatgt ccagctcggt ccagttgctg    420
gtcccattgg taaaattcca gaggtgtgtt tagctggacc ctgtaaagtc ttgcgactga    480
tatcgtacag gccggtcgca actgggaagg cttttctcca gatccatacc tgaatggtct    540
agcaatgtcc aatgtatgtg acgacttctt ccccctaggaa aaggcattga ttggtataga    600
ccattaccgg aatgcaagat gctggcgtac aggcttgtgc aaagcacttt agtaagttgg    660
ttgacggcag ggtcatgcaa gatctgagac tcttcagttg gaaacgagca agaaacgaat    720
cgcgatacaa tgagctccaa catcgatgat cggacttttcc atgaggtagg tgatactcgc    780
aaacaaagat actttggctg atacagatag ttgtacctct ggcctttcgc agatgccatc    840
aaggccaacg ttgcatccat aatgtgctca tacaacaagt tcaatgagac atacgcttgt    900
gagaacaact tcttgacaac tgtaagttct aaggctcgtg catcaattct tcggaatcgc    960
attaacgtct tcagattctc aagggcgagc ttgacttttca aggcttcgtc gtcagcggta   1020
cttggtttcc tatcctgctg ttgaaataag cacagagcta acgcatggtg cgctaagact   1080
gggctgctca gcatactact attggaagtg caaatgctgg tcttgtacgt tgacaaacat   1140
gcgattcata taccattgt agatctcgat cccagcatga actgacacgt tttcaaggat    1200
gttgcgatgc ctggtgacaa ttttggcgac aactattatc tatggggcag caatcttctg   1260
gcggcgatct ccaagtaagt tcctggttcg caaatggcct tgacgttgct gatctctgtg   1320
ccttccatag cggcactgtt gcccaatctc gccttgatga catggtcact cgcatcctgg   1380
cttcatggta ctttgttggt caggaccaag gctatccagc tgtgacctgg tcctcttgga   1440
atggtggatt gggaggtccc aatgtgcagg ctgatcataa gcaggtcgca cgcgccatcg   1500
cccgagatgg cattgtccta ctcacgaaca aaaacaaagc cctgcccctg aagaagcccg   1560
ctagtttagc aatcattggt caagatgcca tcgacaatcc tgcaggcatc aactcgtgct   1620
ccgaccgcgg ttgtgatacg ggtcacttgg ctatggggttg gggctcgggc acagcagact   1680
ttccatacct cgttgcgccg ctcgatgcca tcacacccett agctcaggcc cagggaacaa   1740
agcttgtatt gtcgacgacc gacagtactt ctgccgctgc tagtgctgcc gccgccgcag   1800
agacagcaat cgtcttcatc actgccgatt caggagaggg atacatcact gtgagtttct   1860
ggcatcgagt gctgagcctc tacatttcct aatcagtcac gcacaggttg acggccaatt   1920
```

```
gggtgatcgc aactcacttg ctccatggaa taatggcact gctctcgttc aagcggtagc    1980
cagcgccagc aaaaatgtca ttgtcgtgat caacagtgtc ggcccattga ttctcgagga    2040
cattctcgct ctttccagcg tgaaagcaat tgtctgggct ggcgtctcgg ccaagaatc     2100 gggcaatgga cttgctgata ttctttacgg ttcagtatct cccagtggga aactcccata    2160
cacaatcgcc aaacaggcca gcgactatgg aacagccatt gtgcccggtg acgataactt    2220
tcccgaagga ttgtttgtag actatcgtca tttcgaccaa gcaaacatcc agccgcgttt    2280
tgaatttggc tatggcctct gtaagtccca cccgcgcgcg ttcctttccc ccacgatgat    2340
gataaggaga tgtgatatgt gaagagagtc gaccttctca gccgctgcta tagttagacg    2400
ctaacaaacg tcaacagcct atacgacctt tcaatactcg cagcttaccg caaagtactc    2460
cgatacttcc gcaggcagct ccactctcgc ccctggcgga cccaaggggc tgtatgatat    2520
tgttgcaacg gtaacagcaa aggtgacaaa cagcggcacc gtcagtggcg ctgaagtcgc    2580
acagctatac attggtttgc cgggctcggc gcctgcatct ccacccaagc agctacgcgg    2640
ctttgacaaa atcagcctca agccaggcaa atcaggcacg gtgacgttta acctgcgccg    2700
aaaggacctc agctactggg atactgcctc ggctcagtgg gttacaccga ccagcggcga    2760
gttctccctg tatgttggtg ctagctcgag agatataagg ttacaggggt ctttgaaatg    2820
ctcgggccaa ggtattcgga aaggtggaca t                                   2851
```

<210> SEQ ID NO 4
<211> LENGTH: 740
<212> TYPE: PRT
<213> ORGANISM: Chaetomella raphigera

<400> SEQUENCE: 4

```
Met Tyr Ser Arg Ala Phe Thr Phe Ala Ala Leu Ala Val Pro Ile Leu
1               5                   10                  15

Ala Ala Pro Gly Asp Gly Asp Trp Ala Ala Ala Tyr Lys Lys Ala Thr
            20                  25                  30

Ala Ala Leu Ala Lys Leu Ser Asn Thr Asp Lys Ala Ser Ile Val Thr
        35                  40                  45

Gly Val Gly Trp Glu Lys Gly Pro Cys Val Gly Asn Thr Ala Ala Val
    50                  55                  60

Ala Ser Ile Gly Leu Pro Glu Leu Cys Tyr Gln Asp Gly Pro Leu Gly
65                  70                  75                  80

Ile Arg Phe Val Gln Asn Val Thr Ala Phe Pro Thr Gly Ile Gln Thr
                85                  90                  95

Ala Ser Thr Trp Asp Ile Ser Leu Ile Tyr Ser Arg Gly Leu Ala Leu
            100                 105                 110

Gly Gln Glu Ala Lys Ala Leu Gly Ile Asn Val Gln Leu Gly Pro Val
        115                 120                 125

Ala Gly Pro Ile Gly Lys Ile Pro Glu Ala Gly Arg Asn Trp Glu Gly
    130                 135                 140

Phe Ser Pro Asp Pro Tyr Leu Asn Gly Leu Ala Met Ser Asn Thr Ile
145                 150                 155                 160

Thr Gly Met Gln Asp Ala Gly Val Gln Ala Cys Ala Lys His Phe Ile
                165                 170                 175

Gly Asn Glu Gln Glu Thr Asn Arg Asp Thr Met Ser Ser Asn Ile Asp
            180                 185                 190

Asp Arg Thr Phe His Glu Leu Tyr Leu Trp Pro Phe Ala Asp Ala Ile
        195                 200                 205

Lys Ala Asn Val Ala Ser Ile Met Cys Ser Tyr Asn Lys Phe Asn Glu
```

-continued

```
              210                 215                 220
Thr Tyr Ala Cys Glu Asn Asn Phe Leu Thr Thr Ile Leu Lys Gly Glu
225                 230                 235                 240

Leu Asp Phe Gln Gly Phe Val Val Ser Asp Trp Ala Ala Gln His Thr
                245                 250                 255

Thr Ile Gly Ser Ala Asn Ala Gly Leu Asp Val Ala Met Pro Gly Asp
                260                 265                 270

Asn Phe Gly Asp Asn Tyr Tyr Leu Trp Gly Ser Asn Leu Leu Ala Ala
                275                 280                 285

Ile Ser Asn Gly Thr Val Ala Gln Ser Arg Leu Asp Asp Met Val Thr
290                 295                 300

Arg Ile Leu Ala Ser Trp Tyr Phe Val Gly Gln Asp Gln Gly Tyr Pro
305                 310                 315                 320

Ala Val Thr Trp Ser Ser Trp Asn Gly Gly Leu Gly Gly Pro Asn Val
                325                 330                 335

Gln Ala Asp His Lys Gln Val Ala Arg Ala Ile Ala Arg Asp Gly Ile
                340                 345                 350

Val Leu Leu Thr Asn Lys Asn Lys Ala Leu Pro Leu Lys Lys Pro Ala
                355                 360                 365

Ser Leu Ala Ile Ile Gly Gln Asp Ala Ile Asp Asn Pro Ala Gly Ile
                370                 375                 380

Asn Ser Cys Ser Asp Arg Gly Cys Asp Thr Gly His Leu Ala Met Gly
385                 390                 395                 400

Trp Gly Ser Gly Thr Ala Asp Phe Pro Tyr Leu Val Ala Pro Leu Asp
                    405                 410                 415

Ala Ile Thr Pro Leu Ala Gln Ala Gln Gly Thr Lys Leu Val Leu Ser
                420                 425                 430

Thr Thr Asp Ser Thr Ser Ala Ala Ala Ser Ala Ala Ala Ala Ala Glu
                435                 440                 445

Thr Ala Ile Val Phe Ile Thr Ala Asp Ser Gly Glu Gly Tyr Ile Thr
                450                 455                 460

Val Asp Gly Gln Leu Gly Asp Arg Asn Ser Leu Ala Pro Trp Asn Asn
465                 470                 475                 480

Gly Thr Ala Leu Val Gln Ala Val Ala Ser Ala Ser Lys Asn Val Ile
                    485                 490                 495

Val Val Ile Asn Ser Val Gly Pro Leu Ile Leu Glu Asp Ile Leu Ala
                500                 505                 510

Leu Ser Ser Val Lys Ala Ile Val Trp Ala Gly Val Ser Gly Gln Glu
                515                 520                 525

Ser Gly Asn Gly Leu Ala Asp Ile Leu Tyr Gly Ser Val Ser Pro Ser
530                 535                 540

Gly Lys Leu Pro Tyr Thr Ile Ala Lys Gln Ala Ser Asp Tyr Gly Thr
545                 550                 555                 560

Ala Ile Val Pro Gly Asp Asp Asn Phe Pro Glu Gly Leu Phe Val Asp
                    565                 570                 575

Tyr Arg His Phe Asp Gln Ala Asn Ile Gln Pro Arg Phe Glu Phe Gly
                580                 585                 590

Tyr Gly Leu Ser Tyr Thr Thr Phe Gln Tyr Ser Gln Leu Thr Ala Lys
                595                 600                 605

Tyr Ser Asp Thr Ser Ala Gly Ser Ser Thr Leu Ala Pro Gly Gly Pro
                610                 615                 620

Lys Gly Leu Tyr Asp Ile Val Ala Thr Val Thr Ala Lys Val Thr Asn
625                 630                 635                 640
```

-continued

```
Ser Gly Thr Val Ser Gly Ala Glu Val Ala Gln Leu Tyr Ile Gly Leu
                645                 650                 655

Pro Gly Ser Ala Pro Ala Ser Pro Pro Lys Gln Leu Arg Gly Phe Asp
            660                 665                 670

Lys Ile Ser Leu Lys Pro Gly Lys Ser Gly Thr Val Thr Phe Asn Leu
        675                 680                 685

Arg Arg Lys Asp Leu Ser Tyr Trp Asp Thr Ala Ser Ala Gln Trp Val
690                 695                 700

Thr Pro Thr Ser Gly Glu Phe Ser Leu Tyr Val Gly Ala Ser Ser Arg
705                 710                 715                 720

Asp Ile Arg Leu Gln Gly Ser Leu Lys Cys Ser Gly Gln Gly Ile Arg
                725                 730                 735

Lys Gly Gly His
            740
```

<210> SEQ ID NO 5
<211> LENGTH: 2220
<212> TYPE: DNA
<213> ORGANISM: Chaetomella raphigera

<400> SEQUENCE: 5

```
atgtattccc gagccttcac tttcgcagcc ctagctgtac caatcctagc tgctcctggt      60
gatggtgatt gggcagcggc ttataaaaaa gctaccgctg ctctcgcaaa attgagcaac     120
accgacaaag ccagtattgt tactggcgtg ggttgggaaa agggtccttg cgttgggaat     180
actgctgcag tagcatcaat tggacttcca gagctttgct atcaagatgg acccctaggc     240
atccgtttcg tccaaaatgt aacagcattt cctacaggta ttcagactgc ttccacgtgg     300
gacattagtt tgatctacag tcgaggttta gctttaggtc aggaggcaaa ggcacttggc     360
atcaatgtcc agctcggtcc agttgctggt cccattggta aaattccaga ggccggtcgc     420
aactgggaag cttttctcc agatccatac ctgaatggtc tagcaatgtc caataccatt     480
accggaatgc aagatgctgg cgtacaggct tgtgcaaagc actttattgg aaacgagcaa     540
gaaacgaatc gcgatacaat gagctccaac atcgatgatc ggactttcca tgagttgtac     600
ctctggcctt tcgcagatgc catcaaggcc aacgttgcat ccataatgtg ctcatacaac     660
aagttcaatg agacatacgc ttgtgagaac aacttcttga caactattct caagggcgag     720
cttgactttc aaggcttcgt cgtcagcgac tgggctgctc agcatactac tattggaagt     780
gcaaatgctg gtctggatgt tgcgatgcct ggtgacaatt ttggcgacaa ctattatcta     840
tggggcagca atcttctggc ggcgatctcc aacggcactg ttgcccaatc tcgccttgat     900
gacatggtca ctcgcatcct ggcttcatgg tactttgttg gtcaggacca aggctatcca     960
gctgtgacct ggtcctcttg aatggtgga ttgggaggtc ccaatgtgca ggctgatcat    1020
aagcaggtcg cacgcgccat cgcccgagat ggcattgtcc tactcacgaa caaaaacaaa    1080
gccctgcccc tgaagaagcc cgctagttta gcaatcattg gtcaagatgc catcgacaat    1140
cctgcaggca tcaactcgtg ctccgaccgc ggttgtgata cgggtcactt ggctatgggt    1200
tggggctcgg gcacagcaga ctttccatac ctcgttgcgc cgctcgatgc catcacaccc    1260
ttagctcagg cccagggaac aaagcttgta ttgtcgacga ccgacagtac ttctgccgct    1320
gctagtgctg ccgccgccgc agagacagca atcgtcttca tcactgccga ttcaggagag    1380
ggatacatca ctgttgacgg ccaattgggt gatcgcaact cacttgctcc atggaataat    1440
ggcactgctc tcgttcaagc ggtagccagc gccagcaaaa atgtcattgt cgtgatcaac    1500
agtgtcggcc cattgattct cgaggacatt ctcgctcttt ccagcgtgaa agcaattgtc    1560
```

```
tgggctggcg tctcgggcca agaatcgggc aatggacttg ctgatattct ttacggttca    1620
gtatctccca gtgggaaact cccatacaca atcgccaaac aggccagcga ctatgaaca     1680
gccattgtgc ccggtgacga taactttccc gaaggattgt tgtagacta tcgtcatttc    1740
gaccaagcaa acatccagcc gcgttttgaa tttggctatg gcctctccta tacgaccttt    1800
caatactcgc agcttaccgc aaagtactcc gatacttccg caggcagctc cactctcgcc    1860
cctggcggac ccaaggggct gtatgatatt gttgcaacgg taacagcaaa ggtgacaaac    1920
agcggcaccg tcagtggcgc tgaagtcgca cagctataca ttggtttgcc gggctcggcg    1980
cctgcatctc cacccaagca gctacgcggc tttgacaaaa tcagcctcaa gccaggcaaa    2040
tcaggcacgg tgacgtttaa cctgcgccga aaggacctca gctactggga tactgcctcg    2100
gctcagtggg ttacaccgac cagcggcgag ttctccctgt atgttggtgc tagctcgaga    2160
gatataaggt tacaggggtc tttgaaatgc tcgggccaag gtattcggaa aggtggacat    2220

<210> SEQ ID NO 6
<211> LENGTH: 2905
<212> TYPE: DNA
<213> ORGANISM: Chaetomella raphigera

<400> SEQUENCE: 6
atgtattccc gagccttcac tttcgcagcc ctagctgtac caatcctagc tgctcctggt      60
gatggtgatt gggcagcggc ttataaaaaa gctaccgctg ctctcgcaaa attgagcaac     120
accgacaaag ccagtattgt tactggcgtg gttgggaaa agggtccttg cgttgggaat      180
actgctgcag tagcatcaat tggacttcca gagctttgct atcaagatgg accctaggg     240
taggctgctg gttatttgta gtctcagaac tgacggtgaa agcatccgtt tcgtccaaaa     300
tgtaacagca tttcctacag gtattcagac tgcttccacg tgggacatta gtttgatcta     360
cagtcgaggt ttagctttag gtaagtccaa gtacgctgtc aagatttgaa ttaagagtat     420
taggtcagga ggcaaaggca cttggcatca atgtccagct cggtccagtt gctggtccca     480
ttggtaaaat tccagaggtg tgtttagctg gaccctgtaa agtcttgcga ctgatatcgt     540
acaggccggt cgcaactggg aaggcttttc tccagatcca tacctgaatg gtctagcaat     600
gtccaatgta tgtgacgact tcttccccta ggaaaaggca ttgattggta tagaccatta     660
ccggaatgca agatgctggc gtacaggctt gtgcaaagca ctttagtaag ttggttgacg     720
gcagggtcat gcaagatctg agactcttca gttggaaacg agcaagaaac gaatcgcgat     780
acaatgagct ccaacatcga tgatcggact ttccatgagg taggtgatac tcgcaaacaa     840
agatactttg gctgatacag atagttgtac ctctggcctt tcgcagatgc catcaaggcc     900
aacgttgcat ccataatgtg ctcatacaac aagttcaatg agacatacgc ttgtgagaac     960
aacttcttga caactgtaag ttctaaggct cgtgcatcaa ttcttcggaa tcgcattaac    1020
gtcttcagat tctcaagggc gagcttgact ttcaaggctt cgtcgtcagc ggtacttggt    1080
ttcctatcct gctgttgaaa taagcacaga gctaacgcat ggtgcgctaa gactgggctg    1140
ctcagcatac tactattgga agtgcaaatg ctggtcttgt acgttgacaa acatgcgatt    1200
cataatacca ttgtagatct cgatcccagc atgaactgac acgttttcaa ggatgttgcg    1260
atgcctggtg acaattttgg cgacaactat tatctatggg gcagcaatct tctggcggcg    1320
atctccaagt aagttcctgg ttcgcaaatg gccttgacgt tgctgatctc tgtgccttcc    1380
atagcggcac tgttgcccaa tctcgccttg atgcatggt cactcgcatc ctggcttcat     1440
ggtactttgt tggtcaggac caaggctatc cagctgtgac ctggtcctct tggaatggtg    1500
```

-continued

```
gattgggagg tcccaatgtg caggctgatc ataagcaggt cgcacgcgcc atcgcccgag    1560
atggcattgt cctactcacg aacaaaaaca aagccctgcc cctgaagaag cccgctagtt    1620
tagcaatcat tggtcaagat gccatcgaca atcctgcagg catcaactcg tgctccgacc    1680
gcggttgtga tacgggtcac ttggctatgg gttggggctc gggcacagca gactttccat    1740
acctcgttgc gccgctcgat gccatcacac ccttagctca ggcccaggga acaaagcttg    1800
tattgtcgac gaccgacagt acttctgccg ctgctagtgc tgccgccgcc gcagagacag    1860
caatcgtctt catcactgcc gattcaggag agggatacat cactgtgagt ttctggcatc    1920
gagtgctgag cctctacatt tcctaatcag tcacgcacag gttgacggcc aattgggtga    1980
tcgcaactca cttgctccat ggaataatgg cactgctctc gttcaagcgg tagccagcgc    2040
cagcaaaaat gtcattgtcg tgatcaacag tgtcggccca ttgattctcg aggacattct    2100
cgctctttcc agcgtgaaag caattgtctg gctggcgtc tcgggccaag aatcgggcaa     2160
tggacttgct gatattcttt acggttcagt atctcccagt gggaaactcc catacacaat    2220
cgccaaacag gccagcgact atggaacagc cattgtgccc ggtgacgata actttcccga    2280
aggattgttt gtagactatc gtcatttcga ccaagcaaac atccagccgc gttttgaatt    2340
tggctatggc ctctgtaagt cccacccgcg cgcgttcctt tcccccacga tgatgataag    2400
gagatgtgat atgtgaagag agtcgacctt ctcagccgct gctatagtta dacgctaaca    2460
aacgtcaaca gcctatacga ccttcaata ctcgcagctt accgcaaagt actccgatac     2520
ttccgcaggc agctccactc tcgccctgg cggaccaag gggctgtatg atattgttgc      2580
aacggtaaca gcaaaggtga caaacagcgg caccgtcagt ggcgctgaag tcgcacagct    2640
atacattggt ttgccgggct cggcgcctgc atctccaccc aagcagctac gcggctttga    2700
caaaatcagc ctcaagccag gcaaatcagg cacggtgacg tttaacctgc gccgaaagga    2760
cctcagctac tgggatactg cctcggctca gtgggttaca ccgaccagcg gcgagttctc    2820
cctgtatgtt ggtgctagct cgagagatat aaggttacag gggtctttga aatgctcggg    2880
ccaaggtatt cggaaaggtg gacat                                         2905
```

<210> SEQ ID NO 7
<211> LENGTH: 18
<212> TYPE: PRT
<213> ORGANISM: Chaetomella raphigera

<400> SEQUENCE: 7

Met Tyr Ser Arg Ala Phe Thr Phe Ala Ala Leu Ala Val Pro Ile Leu
1               5                   10                  15

Ala Ala

<210> SEQ ID NO 8
<211> LENGTH: 54
<212> TYPE: DNA
<213> ORGANISM: Chaetomella raphigera

<400> SEQUENCE: 8
atgtattccc gagccttcac tttcgcagcc ctagctgtac caatcctagc tgct    54

<210> SEQ ID NO 9
<211> LENGTH: 7
<212> TYPE: PRT
<213> ORGANISM: Artificial sequence
<220> FEATURE:
<223> OTHER INFORMATION: Synthetic peptide

```
<400> SEQUENCE: 9

Pro Gly Asp Gly Asp Trp Ala
1               5

<210> SEQ ID NO 10
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 10
ccnggngayg gngaytgggc                                              20

<210> SEQ ID NO 11
<211> LENGTH: 39
<212> TYPE: DNA
<213> ORGANISM: Artificial sequence
<220> FEATURE:
<223> OTHER INFORMATION: Synthetic primer

<400> SEQUENCE: 11
ggttcttgcc acagtcacga cttttttttt tttttttt                          39

<210> SEQ ID NO 12
<211> LENGTH: 21
<212> TYPE: DNA
<213> ORGANISM: Artificial sequence
<220> FEATURE:
<223> OTHER INFORMATION: Synthetic primer

<400> SEQUENCE: 12
ggttcttgcc acagtcacga c                                            21

<210> SEQ ID NO 13
<211> LENGTH: 23
<212> TYPE: DNA
<213> ORGANISM: Artificial sequence
<220> FEATURE:
<223> OTHER INFORMATION: Synthetic primer

<400> SEQUENCE: 13
cctggtgatg gtgattgggc agc                                          23

<210> SEQ ID NO 14
<211> LENGTH: 26
<212> TYPE: DNA
<213> ORGANISM: Artificial sequence
<220> FEATURE:
<223> OTHER INFORMATION: Synthetic primer

<400> SEQUENCE: 14
atgtccacct ttccgaatac cttggc                                       26

<210> SEQ ID NO 15
<211> LENGTH: 25
```

```
<212> TYPE: DNA
<213> ORGANISM: Artificial sequence
<220> FEATURE:
<223> OTHER INFORMATION: Synthetic primer

<400> SEQUENCE: 15
cgtttcgtcc aaaatgtaac agcat                                         25

<210> SEQ ID NO 16
<211> LENGTH: 23
<212> TYPE: DNA
<213> ORGANISM: Artificial sequence
<220> FEATURE:
<223> OTHER INFORMATION: Synthetic primer

<400> SEQUENCE: 16
gatgctttca ccgtcagttc tga                                           23

<210> SEQ ID NO 17
<211> LENGTH: 33
<212> TYPE: DNA
<213> ORGANISM: Artificial sequence
<220> FEATURE:
<223> OTHER INFORMATION: Synthetic primer

<400> SEQUENCE: 17
cgcttgaatt cgatgcctgg tgatggtgat tgg                                33

<210> SEQ ID NO 18
<211> LENGTH: 34
<212> TYPE: DNA
<213> ORGANISM: Artificial sequence
<220> FEATURE:
<223> OTHER INFORMATION: Synthetic primer

<400> SEQUENCE: 18
ttcaagcggc cgcatgtcca cctttccgaa tacc                               34
```

BETA-GLUCOSIDASE AND USES THEREOF

CROSS REFERENCE TO RELATED APPLICATIONS

This application is the National Stage of International Application No. PCT/US2011/022906, filed Jan. 28, 2011, which claims the priority of U.S. Provisional Application No. 61/299,007, filed on Jan. 28, 2010. The content of the application is hereby incorporated by reference in its entirety.

BACKGROUND

Developments of alternative energy resources (e.g., solar energy, biofuel, hydropower, wind power etc.) have been encouraged for years to cope with arising energy problems related to vastly consumptions of fossil fuels. Among many possible resources, plant biomass is of particular interest as it is renewable. Plant mass contains a high amount of cellulose, a starting material for making biofuel. To convert cellulose to biofuel, it is first degraded to fermentable sugars, such as cellobiose and glucose, by the cellulolytic system of microorganisms. This system includes three major types of hydrolases, i.e., endoglucanases (EC 3.2.1.4), exoglucanases (EC 3.2.1.91), and β-glucosidases (EC 3.2.1.21). Although many glucosidases have been isolated from various microorganisms, their efficiencies are not satisfactory. Thus, there is a need for a high efficient glucosidase.

SUMMARY

This invention relates to a novel β-glucosidase, BGL-Cr-D2, which is isolated from a Taiwan-indigenous fungus *Chaetomella raphigera*. Shown in FIG. 2 are the sequences of the mature BGL-Cr-D2 protein (722 a.a. resides/SEQ ID NO: 1), the corresponding bgl-Cr-D2 cDNA (2166 bps/SEQ ID NO: 2), the signal peptide sequence (SEQ ID NO: 7), the corresponding cDNA (SEQ ID NO: 8), the BGL-Cr-D2 protein with its signal peptide (SEQ ID NO: 4), and the corresponding cDNA (SEQ ID NO: 5). Shown in FIG. 1 is the genomic DNA region (2851 bps, SEQ ID NO: 3) in *Chaetomella raphigera* encoding the BGL-Cr-D2 enzyme, which contains 12 intron sections, and the genomic DNA region corresponding to SEQ ID NO: 4 (SEQ ID NO: 6).

Accordingly, one aspect of this invention features an isolated polypeptide containing a sequence exhibiting at least 70% (e.g., 80%, 90%, 95%, or 99%) amino acid identity to SEQ ID NO:1 as determined by the BLAST algorithm. In one example, the polypeptide has a β-glucosidase activity.

This invention also encompasses (i) an isolated nucleic acid including a nucleotide sequence that encodes the polypeptide described above, and (ii) a host cell containing such an isolated nucleic acid. In one example, the nucleotide sequence contains the sequence of SEQ ID NO: 2, 3, 5, or 6. The isolated nucleic acid of this invention can be an expression vector, in which the nucleotide sequence is operably linked to a suitable promoter sequence (i.e., a sequence capable of initiating transcription in a host cell).

The term "isolated polypeptide" or "isolated nucleic acid" used herein refers to a polypeptide or nucleic acid substantially free from naturally associated molecules, i.e., the naturally associated molecules constituting at most 20% by dry weight of a preparation containing the polypeptide or nucleic acid. Purity can be measured by any appropriate method, e.g., column chromatography, polyacrylamide gel electrophoresis, and HPLC.

Also within the scope of this invention are (A) a composition containing the polypeptide described above, an exoglucanase, an endo-glucanase, and/or a β-glucosidase, and (B) a method of producing a fermentable sugar from a ligocellulosic material. The method includes (i) providing the just-described composition, and (ii) contacting this composition with a lignocellulosic material to produce a fermentable sugar, e.g., glucose, xylose, arabinose, galactose, mannose, rhamnose, surose, fructose, lactose, maltose, trehalose, or cellobiose. The fermentable sugar can be converted to a fermentation product, such as alcohol, by microbial fermentation or enzyme treatment. Examples of the lignocellulosic material used in this method include, but are not limited to, orchard prunings, chaparral, mill waste, urban wood waste, municipal waste, logging waste, forest thinnings, short-rotation woody crops, industrial waste, wheat, wheat straw, oat straw, rice straw, barley straw, rye straw, flax straw, soy hulls, rice hulls, oat hulls, sugar cane, corn, corn stover, corn stalks, corn gluten feed, corn cobs, corn husks, corn kernel, fiber from kernels, prairie grass, gamagrass, foxtail, sugar beet pulp, citrus fruit pulp, seed hulls, cellulosic animal wastes, lawn clippings, cotton, seaweed, trees, shrubs, grasses, sugar cane bagasse, products and by-products from wet or dry milling of grains, municipal solid waste, waste paper, yard waste, herbaceous material, agricultural residues, forestry residues, municipal solid wastes, waste paper, pulp, paper mill residues, branches, bushes, canes, corn, corn husks, energy crops, forests, fruits, flowers, grains, grasses, herbaceous crops, leaves, bark, needles, logs, roots, saplings, shrubs, switch grasses, trees, vegetables, fruit peels, vines, sugar beet pulp, wheat midlings, oat hulls, hard and soft woods, organic waste materials generated from agricultural processes, forestry wood waste, or combinations thereof. If the fermentation product is combustible, the method further contains a step of combusting the combustible fermentation product to produce energy.

This invention also features a bioreactor containing a lignocellulosic material and a composition, including the polypeptide described above, an exo-glucanase, an endo-glucanase, and/or a β-glucosidase.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a diagram showing the bgl-Cr-D2 cDNA (2166 bps/SEQ ID NO: 2 excluding signal sequence indicated with underline/SEQ ID NO: 8) and its encoding amino acid sequences (722 a.a. resides/SEQ ID NO: 1, excluding signal peptide/SEQ ID NO: 7) for a Taiwan-indigenous fungus *Chaetomella raphigera*.

DETAILED DESCRIPTION

Figure 1:
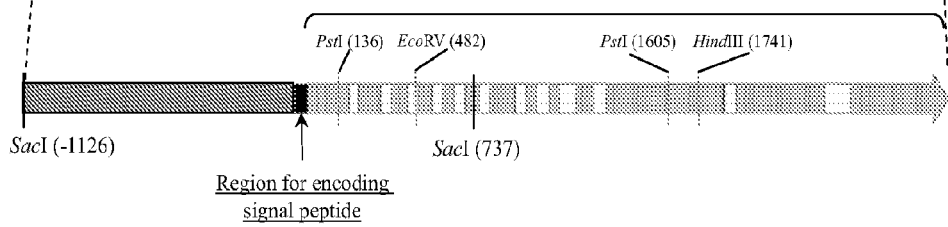
FIG. 1 is a diagram showing the genomic DNA region (2851 bps, SEQ ID NO: 3) in *Chaetomella raphigera* encoding the BGL-Cr-D2 enzyme, which contains 12 intron sections (as indicated with "White" sections in the diagram and "Small Caps/Gray/Strikethrough" sections in the sequence). A region encoding signal peptide is indicated with "Black" in the diagram and "Underline" in the sequence.

This invention is based, at least in part, on the unexpected discoveries of a novel beta-glucosidase and its high enzymatic activity or efficiency. Beta-glucosidases (or beta-D-glucoside glucohydrolase, BGL) are a group of the key enzymes for processing lignocellulosic saccharization. This type of enzyme can liberate D-glucose units from the cellulose-hydrolyzing media such as cellobiose, cello-oligosaccharides, and other glucosides after the actions of endo-glucanases (EG) (mainly degrading the amorphous parts of cellulose fiber) and exo-glucanases (or cellobiohydrolases, CBH) (mainly degrading the crystalline cellulose). For industrial-scale production of biofuel from lignocelluloses, finding low-cost cellulases (i.e., CBH, EG, and BGL) with high activity and productivity is essential.

This invention discloses new discoveries in polypeptides with beta-glucosidase activity, polynucleotides encoding the polypeptides, and enhancement in beta-glucosidase specific activity for recombinant beta-glucosidase expressed from yeast. Explicitly, a Taiwan-indigenous fungus, i.e., *Chaetomella raphigera* strain D2, was found capable of secreting an active beta-1,4-glucosidase (BGL-Cr-D2). The gene (bgl-Cr-D2, size=2166 bps) encoding this enzyme was cloned from reverse-transcribed cDNA and has been successfully expressed in a yeast expression system using *Pichia pastoris* strain SMD1168 as the host. Recombinant enzyme BGL-Cr-D2-Pp secreted from *P. pastoris* had a higher β-glucosidase activity (based on pNPGase activity measurement) than the native enzyme (approx. 3×) and the benchmark Novozyme-188 (approx. 17×). This invention provides a new recombinant β-glucosidase enzyme that has potential to be utilized together with other cellulases for cellulosic saccharization.

1. Biofuels from Lignocellulose

Developments of renewable power resources (e.g., solar energy, biofuel, hydropower, wind power etc.) have been encouraged for years to cope with arising energy problems related to vastly consumptions of fossil fuels. Among the currently-exploited renewable energy forms/sources, biofuel has a unique advantage in reducing agricultural/municipal/industrial organic wastes while generating cleanliness and energy-rich fuels (e.g., methane, ethanol, butanol, and hydrogen). Thus, it has been listed as one of important sustainable energies (Antoni et al., 2007, Appl Microbiol Biotechnol 77:23-35; and Rubin, 2008, Natures 454:841-845). Not only in Taiwan, production of bioethanol from lignocellulose is urgent worldwide as about $5 \times 10^{12}$ tons of cellulose-rich agriculture wastes are produced on the earth every year and supplement of ethanol in gasoline is ongoing or on-its-way in many countries. Prior to further fermentation for ethanol production, various enzyme systems (e.g., ligninase, cellulases, and hemicellulases) are required for complete breakdown of lignocelluloses (containing about 5-30% of lignin, approximately 35-50% of cellulose, and approximately 20-35% of hemicellulose) to release fermentable glucose (Lynd et al., 2002, Microbiol Mol Biol Rev 66:506-577).

2. Cellulases

For bioethanol production from cellulose, efficient saccharification (degradation of polymeric cellulose fibers to release smaller glucose molecules) by cellulases is crucial. Cellulases are a group of enzymes responsible for complex cellulose hydrolysis. Multiple cellulases have been classified into three groups, i.e., (i) exoglucanases (including 1,4-β-D-glucan cellobiohydrolases, CBH, EC 3.2.1.91 and 1,4-β-D-glucan glucanohydrolases, EC 3.2.1.74), (ii) endoglucanases (EG) (EC 3.2.1.4), and (iii) beta-glucosidases (or β-D-glucoside glucohydrolase, BGL) (EC 3.2.1.21) based on structural and functional properties of the enzymes (Coughlan et al., 1988, In Biochemistry and Genetics of Cellulose Degradation, pp. 11-30; and Henrissat et al., 1989, Gene 81:83-95). The CBH mainly act on the crystalline sections at reducing or nonreducing end of cellulose fiber while EG randomly attack the amorphous parts of cellulose. More specifically, these cellulases can cleave the β-1,4-glucan or β-D-glucosidic linkages between glucosyl residues within celluloses to form short-chain media including cellobiose (i.e., disaccharides), other cellodextrins (i.e., cello-oligosaccharides), and glucosides (e.g., alcoholic, cyanogenic, or phenolic glycosides). These short-chain intermediates can be further hydrolyzed to glucose (i.e., monosaccharide) by BGL that primarily catalyzes the transfer of glycosyl group between oxygen nucleophiles (Bhatia et al., 2002, Crit. Rev Biotechnol 22(4):375-407). For cellulose saccharification, insufficient BGL activity can result in not only shortage of glucose but also accumulation of cellobiose that is a potent inhibitor for cellulose hydrolysis by CBH and EG (Harris et al., 2007, U.S. Pat. No. 7,244,605B2). Thus, BGL plays an important role in achieving high ethanol yield from cellulose (Lynd et al., 2002, Microbiol Mol Biol Rev 66:506-577; and Hong et al., 2007, Appl Microbiol Biotechnol 73:1331-1339).

3. Sources of β-Glucosidases (BGLs)

The enzyme BGL is ubiquitous and has been discovered in all the living kingdoms from microbes, insects, and plants to highly-evolved mammals (Esen, 1993, In Biochemistry and Molecular Biology, American Chemical Society, 1-14; Bhatia et al., 2002, Crit. Rev Biotechnol 22(4):375-407). One of major BGL-producing sources is from bacteria including some strains of genus *Agrobacterium, Bacillus, Butyrivibrio, Cellovibrio, Clostridium, Erwinia, Pseudomonas, Pyrococcus, Ruminococcus, Streptomyces, Thermotoga, Thermobifida* etc. (Hashimoto et al., 1998, Arch Biochem Biophys 360:1-9; Srivastava et al., 1999, Biotechnol Lett 21:293-297; and Yun et al., 2001, Biosci Biotechnol Biochem 65(9):2028-2032). Fungal strains (molds or yeasts) with BGL-producing ability include those from genus *Aspergillus, Candida, Humicola, Penicillium, Pichia, Saccharomycopsis, Talaromyces, Trichoderma* etc. (Dan et al., 2000, J Biol Chem 275(7):4973-4980; and Dunn-Coleman et al., 2008, U.S. Patent Publication 2008/0095889A1). Among these microbes, fungal species *Aspergillus niger, Aspergillus fumigates*, and *Trichoderma reesei* are the most well-known and efficient BGL producers making them the major sources for commercial BGLs in the world (Dan et al., 2000, J Biol Chem 275 (7):4973-4980; Harris et al., 2007, U.S. Pat. No. 7,244,605B2; and Dunn-Coleman et al., 2008, U.S. Patent Publication 2008/0095889A1). In addition, few plants like barley, *Costus*, and Maize have been found containing BGL as well.

Beside above-mentioned native sources, some recombinant BGLs have been expressed in different hosts (e.g., *E. coli, B. subtilis, P. pastoris, S. cerevisiae, A. kawachii*, and *T. reesei*) (Pandey et al., 1995, J Ferment Bioeng 80(5):446-453; Murray et al., 2004, Protein Expres Purif 38:248-257; and Roy et al., 2005, Biochem Bioph Res Co 336:299-308). For example, bgl genes from *Bacillus* sp. had been successfully cloned and expressed in *E. coli* system (Hashimoto et al., 1998, Arch Biochem Biophys 360:1-9; and Srivastava et al., 1999, Biotechnol Lett 21:293-297). In addition, an *Aspergillus niger* BGL coding gene, bgl1, had been expressed in *P. pastoris* and *S. cerevisiae* (Dan et al., 2000, J Biol Chem 275(7):4973-4980). Clone BGL genes from diverse sources and then express in different hosts has been a practical approach for gaining higher BGL productivity (over-expression) and/or activity (advantageous post-translational modification improve kinetic features of the enzymes).

4. Properties of BGLs

The properties of BGLs are rather diverse by far. In general, BGLs from different orders and kingdoms appear to differ in their specificities for the aglycone part (aryl-, alkyl-, or amino-) linked to the glycosyl group (Bhatia et al., 2002, Crit. Rev Biotechnol 22(4):375-407). They have been found to be intracellular, extracellular, cytosol-associated, membrane-bound, or periplasmically-localized. Their catalytic functionalities on hydrolyzing short-chain cellobiose and oligosaccharides are quite similar in cellulosic microorganisms although some other various functions have been noticed in different organisms (e.g., synthesis of glycosyl-bond between different molecules in some microbes, releasing cyanides from cyano-glucoside precursors in insects and plants, and hydrolysis of glycosylceramides for treating Gaucher's disease in humans) (Bhatia et al., 2002, Crit. Rev Biotechnol 22(4):375-407). For cellulose hydrolysis, BGLs are able to hydrolyze their substrates with net retention of anomeric configuration that occurs presumably via a two-step, double-displacement mechanism involving two carboxylic acid residues at key active site (Davies et al., 1998, Comprehensive Biological Catalysis Vol. 1, pp. 119-208; and Withers, 2001, Carbohyd Polym 44:325-337). It has been noted that most of BGLs have different substrate specificity and can act on a wide spectrum of substrates (e.g., pNPG; cellobiose, salicin, MUG, arbutin, aryl-, alkyl-, and methyl-glucosides). In addition, most of BGLs have optimum pH within weak-acid levels and optimum temperature in mesophilic scopes despite some strong-acid and/or thermophilic properties have been reported. The BGL monomers from diverse organism sources have a very broad molecular size range (i.e., about 13-137 kDa) (Gabelsberger et al., 1993, Appl Microbiol Biotechnol 40:44-52; Iwashita et al., 1999, Appl Environ Microbiol 65:5546-5553; Srivastava et al., 1999, Biotechnol Lett 21:293-297; and Dan et al., 2000, Biol Chem 275(7):4973-4980). Amino acid sequence similarities between BGLs of different organism species also vary widely (10 s-90 s %). Nevertheless, amino acid bases of aspartic acid (Asp, D) and glutamine acid (Glu, E) have been recognized as catalytic necleophile and catalytic proton donor of BGLs.

5. Classification of BGLs

Based on chemical reactions they catalyze, all BGLs have been assigned to EC 3.2.1.21 category (i.e., Enzyme Commission number of 3-hydrolases, 2-glycosylases, 1-glycosidases, and 21-glucosidase) according to numerical classification scheme for more than 3,000 enzymes published by the IUBMB (International Union of Biochemistry and Molecular Biology) (Webb, 1992, Enzyme nomenclature: recommendations of the Nomenclature Committee of the International Union of Biochemistry and Molecular Biology on the nomenclature and classification of enzymes, ISBN 0-12-227164-5; and ExPASy, 2009, www.expasy.org/enzyme/). Additionally, BGLs are versatile hydrolytic enzymes that have been further classified according to various criteria (e.g., substrate specificity and sequence identity). At first, BGLs had been grouped into Type I and II (Beguin et al., 1990, Ann Rev Microbiol 44:219-248) or subfamily A and B (Rojas et al., 1995, Biochem Mol Biol Int 35:1223-1231); but lately, these earlier classifications have been mostly replaced by the currently-acceptable scheme based on amino acid and/or nucleotide sequence identity (Henrissat et al., 1996, Biochem J 316:695-696).

Based on amino acid sequence and folding similarities, the BGLs have been placed in either family 1 or 3 among 115 up-to-date (November 2009) defined GH (glycoside-hydrolases) families with an exception of the glucosylceramidases (i.e., acid β-glucosidase placed in family 30) (Henrissat, 1991, Biochem J 280:309-316; Henrissat et al., 1993, Biochem J 293:781-788; Henrissat et al., 1996, Biochem J 316: 695-696; Hong et al., 2007, Appl Microbiol Biotechnol 73:1331-1339; and Cantarel et al., 2009, Nucleic Acids Res. 37:D233-238). Family 1 (GH1) contains β-glucosidases from some archaea, bacteria, fungi, plants, and mammals whereas family 3 (GH3) comprises β-glucosidases of some bacterial, fungal, and plant origins (Henrissat et al., 1996, Biochem J 316:695-696; and Cantarel et al., 2009, Nucleic Acids Res. 37:D233-238).

6. Applications

Beside cellobiose/cellodextrins hydrolysis function used for cellulosic ethanol production, BGLs also can be broadly used in the fields of medicine, agriculture, and food industry wherein many reactions engaging cleavage or synthesis of glycosidic bonds are required. Applications based on hydrolytic activities of BGLs include (1) removal of bitterness from citrus fruit juices, (2) manufacture of low-viscosity gellan foods, (3) detoxification of cassaya (the $3^{rd}$-$4^{th}$ largest source of calories in the tropics), (4) enhancement of aroma release for benefiting winemaking process, (5) feed additive for enhancing nutrient utilization in single-stomached animals, (6) hydrolysis of genistin to genistein as an antitumor agent, (7) production of melanin from phloridzin for reducing the risk of skin cancer and promoting dark color of hair, (8) production of hydroxytyrosol from oleuropein for preventing coronary heart disease and cancer, (9) hydrolysis of laminarin for the production of yeast extract and the conversion of algal biomass to fermentable sugars, (10) making pigments as natural food dyes in confectionary products, etc. (Bhatia et al., 2002, Crit. Rev Biotechnol 22(4):375-407).

In addition, synthetic activities of BGLs have been widely used in the manufacture of pharmaceuticals, fine chemicals and food ingredients (as summarized by Bhatia et al., 2002, Crit. Rev Biotechnol 22(4):375-407). For instance, synthesis of an aromatic n-alkyl glucoside ester that was effective in the treatment of fever, rheumatism, headache, and other ailments (Otto et al., 1998, Biotechnol Lett 20:437-440). Other applications of BGLs also have been reported such as sero-diagnosing histoplasmosis or post-diagnosing hepatic ischemia-reperfusion injury and recovery. Therefore, productions of high quality/quantity BGLs from diverse sources have been fundamental tasks for these multipurpose applications.

Described herein is an isolated polypeptide including an amino acid sequence at least 70% identical to that of BGL-Cr-D2 (SEQ ID NO:1) or a part thereof having at least 20 (e.g., 30, 50, 80, 100, 150, 200, 250, 300, and 350) contiguous amino acids. This polypeptide has a high beta-glucosidase activity.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The isolated polypeptide can be prepared by purification from a suitable microorganism, e.g., *Chaetomella raphigera*. It also can be prepared via conventional recombinant technology. An example follows. A DNA fragment encoding BGL-Cr-D2 can be prepared by polymerase chain reaction from *Chaetomella raphigera* cells and cloned into an expression vector. Upon insertion, the BGL-Cr-D2-encoding fragment is operably linked to a suitable promoter contained in the expression vector. The resultant DNA construct is then introduced into suitable host cells (e.g., *E. coli* cells, yeast cells, insect cells, and mammalian cells) for expression of BGL-Cr-D2, which can be purified from the cells by conventional methods. One example of yeast cells is *Pichia pastoris*, e.g., *Pichia pastoris* strain SMD1168.

To make a functional equivalent of BGL-Cr-D2, which is also within the scope of this invention, one or more conservative amino acid substitutions can be introduced into SEQ ID NO:1 without disrupting its β-glucosidase activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the β-glucosidase activity to identify mutants that retain the activity as descried below in the Example section below.

Fusion protein technology can be applied to improve expression efficiency and facilitate purification of the polypeptide of this invention. To prepare a fusion protein containing BGL-Cr-D2, a DNA fragment encoding this β-glucosidase can be linked to another DNA fragment encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Also described herein is an isolated nucleic acid encoding the polypeptide of this invention. A nucleic acid refers to a DNA molecule (e.g., a cDNA or genomic DNA), an RNA molecule, or a DNA/RNA analog, which can be synthesized from nucleotide analogs. In one example, the nucleic acid of this invention is an expression vector in which a DNA fragment encoding the polypeptide is operably linked to a suitable promoter.

As used herein, the term "promoter" refers to a nucleotide sequence containing elements that initiate the transcription of an operably linked nucleic acid sequence in a desired host microorganism. At a minimum, a promoter contains an RNA polymerase binding site. It can further contain one or more enhancer elements which, by definition, enhance transcription, or one or more regulatory elements that control the on/off status of the promoter. When *E. coli* is used as the host microorganism, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al., *Gene* 20:231-243, 1982). When yeast is used as the host microorganism, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of cells are also well known in the art.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleotide sequence encoding BGL-Cr-D2 in a form suitable for expression of the nucleic acid in a host cell. Preferably the vector includes one or more regulatory sequences operatively linked to the encoding sequence. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention.

Also within the scope of this invention is a host cell that contains the above-described nucleic acid. Examples include E. coli cells, insect cells (e.g., using baculovirus expression vectors), yeast cells, plant cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

Further described herein is a method of converting lignocellulosic material to fermentable products (e.g., fermentable sugars) using a multi-enzyme composition containing the β-glucosidase described herein and other cellulolytic enzymes, such as exo-glucanase and endo-glucosidase. See, e.g., US Application Nos. 20070238155 and 20070250961. The term "cellulolytic enzyme" refers to an enzyme that hydrolyzes cellulose (a polysaccharide consisting of glucose units) into smaller sugar units. See Gilbert H J, Hazlewood G P, 1993 J Gen Microbiol 139:187-194; Olimiya K et al. 1997 Biotechnol Genet Eng Rev. 14:365-414. See also, e.g., US Application 2007016805. This multi-enzyme composition can be obtained from, e.g., a microbial, a plant, or a combination thereof, and will contain enzymes capable of degrading lignocellulosic material. In addition to the cellulolytic enzymes mentioned above, it can further include cellobiohydrolases, endoglucanase, beta.-glucosidases), hemicellulases (such as xylanases, including endoxylanases, exoxylanase, and beta-xylosidase), ligninases, amylases, alpha-arabinofuranosidases, alpha-glucuronidases, alpha-glucuronidases, arabinases, glucuronidases, proteases, esterases (including ferulic acid esterase and acetylxylan esterase), lipases, glucomannanases, or xylogluconases.

As used herein the term "lignocellulosic material" refers to materials containing cellulose and/or hemicellulose. Generally, these materials also contain xylan, lignin, protein, and carbohydrates, such as starch and sugar. Lignocellulose is found, for example, in the stems, leaves, hulls, husks, and cobs of plants or leaves, branches, and wood of trees. The process of converting a complex carbohydrate (such as starch, cellulose, or hemicellulose) into fermentable sugars is also referred to herein as "saccharification." Fermentable sugars, as used herein, refer to simple sugars, such as glucose, xylose, arabinose, galactose, mannose, rhamnose, surose, fructose, lactose, maltose, trehalose, or cellobiose. Lignocellulosic material can include virgin plant biomass and/or non-virgin plant biomass such as agricultural biomass, commercial organics, construction and demolition debris, municipal solid waste, waste paper, and yard waste. Common forms of lignocellulosic material include trees, shrubs and grasses, wheat, wheat straw, sugar cane bagasse, corn, corn husks, corn kernel including fiber from kernels, products and by-products from milling of grains such as corn, rice, wheat, and barley (including wet milling and dry milling), as well as municipal solid waste, waste paper, and yard waste. The lignocellulosic material can also be, but is not limited to, herbaceous material, agricultural residues, forestry residues, and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, hard and soft woods (not including woods with deleterious materials), organic waste materials generated from agricultural processes including farming and forestry activities, specifically including forestry wood waste, or a mixture thereof.

The fermentable sugar produced in the method described above can be converted to useful value-added fermentation products via enzyme treatment or chemical reaction. Examples of the fermentation product include, but are not limited to amino acids, vitamins, pharmaceuticals, animal feed supplements, specialty chemicals, chemical feedstocks, plastics, solvents, fuels, or other organic polymers, lactic acid, and ethanol, including fuel ethanol. Specific value-added fermentation products that may be produced by the methods of the invention include, but not limited to, biofuels (including ethanol and butanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; chemical feedstocks. The fermentable sugar can also be used for culturing microbes that produce fermentation products, e.g., industrial enzymes, such as proteases, cellulases, amylases, glucanases, lactases, lipases, lyases, oxidoreductases, transferases and xylanases.

The invention also provides a method of producing energy from lignocellulosic material. This method include providing the multi-enzyme composition described above; contacting the composition with the lignocellulosic material to produce a fermentable product; fermenting the fermentable product to produce a combustible fermentation product, and combusting the combustible fermentation product to produce energy. This method can be performed in a bioreactor that contains all necessary components and may preferably be configured for anaerobic growth of microorganisms. Methods for making and using bioreactors are known in the art. See, e.g., US Application 20080131958.

The polypeptide and composition described above can also be used in the paper and pulp industry. For example, the polypeptide, which has a high β-glucosidase activity can be used in the deinking and refining of recycled paper. In this application, utilizing of them could reduce the amount of enzyme used per ton of paper substantially, and reduce the time of exposure to the enzyme needed to increase the brightness of the paper. Reducing the concentration of enzyme and the time of exposure to the enzyme in the refining process, correspondingly and desirably reduces the reaction of the cellulase on the fibrils themselves and processing costs.

The polypeptide of this invention has additional industrial applications. Given its high β-glucosidase activity, this polypeptide can function at a lower amount. The polypeptide, in combination with other enzymes, can be used, with enhanced yields, in extracting juice from fruits, or extracting juice or soup flavorings from vegetables. In combination with protease, it can be used to dissociate dried seaweed, which is then fermented with alcohol to produce vinegar. The polypeptide, mixed with other enzymes, can also serve as a dough conditioner in the baking industry. See, e.g., U.S. Pat. No. 6,602,700.

Moreover, the polypeptide of this invention can also be used in the textile industry. It can be used to brighten and soften cotton fabrics by removing microfibers on the surface, which causes a dull look of clothes. More specifically, it can be included as an additive in formulating enzyme-containing detergents for soil removal, fabric softening, and color brightening. For example, it can be used as a replacement to pumice in producing blue jeans having a "stone-washed" effect. Enzyme treatment causes less damage to the jean fabric than lengthy exposure to pumice. See U.S. Pat. Nos. 5,232,851, 5,677,151, 6,451,063, and 7226773.

In another aspect, the present invention provides a transgenic plant, the genome of which is augmented with a recombinant polynucleotide encoding a polypeptide of this invention operably linked to a promoter sequence. The polynucleotide is optimized for expression in the plant and the polypeptide is produced at a level greater than 5% total soluble protein, greater than 10% total soluble protein or greater than 20% total soluble protein. The polypeptide may be expressed constitutively or tissue-specifically. For example, it may be expressed in a plant tissue selected from the group consisting of stems and leaves. It may also be expressed in a targeted sub-cellular compartment or organelle, such as apoplast, chloroplast, cell wall, or vacuole. The plant may be a monocotyledonous plant or a dicotyledonous plant. In certain embodiments, the plant is a crop plant. The plant may be selected from the group consisting of corn, switchgrass, sorghum, miscanthus, sugarcane, poplar, pine, wheat, rice, soy, cotton, barley, turf grass, tobacco, bamboo, rape, sugar beet, sunflower, willow, and eucalyptus. Methods for making transgenic plants are well known in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

I. Materials and Methods

1. Cultivation of Native D2 Fungal Strain

The native fungal strain (i.e., *Chaetomella raphigera* D2) was cultured with MR (Mendels-Reese) medium (pH 5.0) to harvest fungal cells for DNA/RNA extractions and their crude enzymes for property analyses (e.g., amino acid sequences, cellulosic activities, and enzyme concentrations). Each one-liter MR medium contains 1 g soy peptone, 1.4 g $(NH_4)_2SO_4$, 0.3 g urea, 2.0 g $KH_2PO_4$, 0.34 g $CaCl_2$, 0.3 g $MgSO_4O.7H_2O$, 5.0 mg $FeSO_4.7H_2O$, 1.6 mg $MnSO_4.7H_2O$, 1.4 mg $ZnSO_4.7H_2O$, 2 mg $CoCl_2.6H_2O$, and 0.72 g cellobiose. Fungal culture was grown at a temperature of 30° C. and a mixing rate of 125 rpm for 4 days prior to gather fungal cells and their crude enzymes.

2. Nucleic Acid Extraction and Crude Enzyme Collection

Genomic DNA of the *C. raphigera* D2 fungus was extracted using Wizard® Genomic DNA Purification Kit (Promega, USA) and fungal RNA was extracted using Plant Total RNA Miniprep Purification Kit (GeneMark, Taiwan). Concentrations of extracted nucleic acid were measured by a spectrophotometer (NanoDrop ND-1000, Thermo Scientific, USA). The DNA and RNA extracts were stored at −20° C. prior to further treatments (e.g., PCR and RT PCR) were conducted.

Crude enzymes were collected by filtering supernatant of 4-day fungal culture through Whatman No. 1 filter paper (Whatman/GE Healthcare, USA), then 0.45 μm Supor® Membrane Disc Filter (PALL, USA), and followed by 30K NMWL (Nominal Molecular Weight Limit) Amico® Ultra-15 Centrifugal Filter (Millipore, USA). Enzyme concentrations were determined based on Bio-Rad Protein Assay using BSA (bovine serum albumin) as calibration standard (Bio-Rad, USA). The filtered enzymes were stored at 4° C. until further analyses were conducted.

3. Enzyme Electrophoresis and N-Terminal Sequencing

Enzyme electrophoreses including native PAGE (polyacrylamide gel electrophoresis) and SDS (sodium dodecylsulfate) PAGE were performed based on the protocols suggested by Hoefer's Protein Electrophoresis Applications Guide (Hoefer Scientific Instruments, 1994). Before Coomassie blue staining for native PAGE, zymogram was carried out by immersing gel with 0.5 mM MUG (4-Methylumbelliferyl β-D-glucopyranoside) solution and incubating at 50° C. for 15 minutes and then followed by observation under UV light (Benoit et al., 1995, Curr Microbiol 30:305-312). Additionally, instead of coomassie blue staining for SDS-PAGE, silver staining using PlusOne Silver Staining Kit (GE Healthcare, USA) was also performed for observing some enzymes with low concentration.

For N-terminal sequence analysis, the target enzyme (i.e., BGL with MUG activity) was transferred from SDS-PAGE gel to PVDF membrane (iBlot Gel Transfer Stacks, Invitrogen, USA) and analyzed by Applied Biosystems Procise Protein Sequencer model 494 (Applied Biosystems, USA) based on Edman degradative chemistry. Part of the revealed N-terminal sequence, PGDGDWA (SEQ ID NO: 9), was used to design a degenerate primer D2-bgl-NT: CCN GGN GAY GGN GAY TGG GC (SEQ ID NO: 10) for further amplifying target bgl gene from genomic DNA and/or reverse transcribed cDNA.

4. Cloning and Sequencing for D2-bgl Gene

The bgl-Cr-D2 cDNA was first reverse transcribed (RT) from RNA sample using a poly-T primer: GGT TCT TGC CAC AGT CAC GAC TTT TTT TTT TTT TTT TTT (SEQ ID NO: 11) and SuperScript® III Reverse Transcriptase (Invitrogen, USA); and, subsequently amplified using a primer set of D2-bgl-NT and poly-T anchor primer: GGT TCT TGC CAC AGT CAC GAC (SEQ ID NO: 12) and a DNA polymerase (TaKaRa Ex Taq™, TaKaRa Bio Inc, Japan). PCR thermo-cycle conditions were 94° C. for 4 minutes, followed by 30 cycles at 94° C. for 1 minute, 58° C. for 30 seconds, and 72° C. for 3 minutes, and then a final elongation at 72° C. for 5 minutes. The RT-PCR product (i.e., amplicon of bgl-Cr-D2 cDNA) was cloned in pGEM®-T Easy vector (Promega, USA) and transferred into *E. coli* cells (strain DH5α) for preservation and further sequencing. Besides, the bgl-Cr-D2 gene (containing introns) was amplified from genomic DNA sample using a primer set of D2-bgl-f: CCT GGT GAT GGT GAT TGG GCA GC (SEQ ID NO: 13) and D2-bgl-r: ATG TCC ACC TTT CCG AAT ACC TTG GC (SEQ ID NO: 14) and TaKaRa Ex Tag™. The PCR product was also cloned in pGEM®-T Easy vector for sequencing. Intron sections were determined by comparing bgl-Cr-D2 cDNA (without introns) and bgl-Cr-D2 genomic DNA (with introns) sequences.

Additionally, signal sequence upstream of the bgl-Cr-D2 gene was revealed by randomly digesting genomic DNA with SacI restriction enzyme (NEB, New England Biolabs Inc., USA) and self-ligation with T4 DNA ligase (Promega, USA); and then, followed by inverse PCR using a primer set of D2-bgl233f: CGT TTC GTC CAA AAT GTA ACA GCA T (SEQ ID NO: 15) and D2-bgl232r: GAT GCT TTC ACC GTC AGT TCT GA (SEQ ID NO: 16). The PCR program was as follow: 5 minutes at 95° C., followed by 25 cycles consisting of 1 minute at 95° C., 1 minute at 55° C., and 6 minutes at 72° C. and a final cycle consisting of 10 minutes at 72° C. The inverse PCR product (should contain a sequence in the order of D2-bg1233f+partial D2-bgl+SacI+partial D2 genome+ signal sequence of D2-bgl+partial D2-bgl+D2-bg1232r) was cloned in pGEM®-T Easy vector for further sequencing.

The putative amino acid sequence of BGL-Cr-D2 from revealed bgl-Cr-D2 cDNA was aligned with other GH3 family BGLs using Clustal X software (Thompson et al., 1997, Nucleic Acids Research 25(24): 4876-4882) to analyze phylogenetic relationships. The alignment result was used to build phylogenetic tree that was visualized in TreeView (Page, 1996, Computer Applications in the Biosciences 12:357-358).

5. Expression in *Pichia pastoris*

The bgl-Cr-D2 cDNA (cloned in the pGEM®-T Easy Vector) was further constructed in pGAPZα C vector for constitutive expression of recombinant BGL-Cr-D2-Pp in *Pichia* yeast (Invitrogen, USA). Briefly, the bgl-Cr-D2 cDNA in the Easy vector was PCR amplified with a primer set of D2-bgl-f-EcoRI: CGC TTGAATTCG ATG CCT GGT GAT GGT GAT TGG (SEQ ID NO: 17) and D2-bgl-r-NotI: TTC AA GCGGCCGCAT GTC CAC CTT TCC GAA TAC C (SEQ ID NO: 18). This PCR product was joined into the pGAPZα C vector by double digesting amplicon and vector with EcoRI and NotI (NEB, USA) and then ligation with T4 DNA ligase. The constructed pGAPZα C vector carrying bgl-Cr-D2 cDNA was transformed into *E. coli* (strain DH5α) for preservation. Prior to subsequently transforming into *Pichia* host, the pGAPZα C vector with D2-bgl cDNA was purified with Plasmid Miniprep Purification Kit (GeneMark, Taiwan) and linearized with BspHI (NEB, USA). The linear plasmid DNA was transformed into *Pichia pastoris* (strains GS115 and SMD1168) via homologous recombination based on protocol for *Pichia* Expression Kit (Invitrogen, USA). The reconstructed *Pichia pastoris* yeast cells were grown in YPD$_{zeocin100}$ medium and the conditions (e.g., 30° C. and 200 rpm) suggested in the Invitrogen protocol. *Pichia* cells and their enzymes were collected at different time points (0-14 days) to assess their growth and enzyme activity/quantity.

6. Activity Tests

Cellulolytic activities of crude enzymes from native D2 strain and recombinant enzymes from *Pichia pastoris* were tested using different substrates (p-nitrophenyl glucopyranoside, pNPG; cellobiose; carboxymethylcellulose, CMC; xylan; avicel; and, filter paper). The pNPGase activities of the enzymes were measured based on pNP releasing rate from 2 mM pNPG at 55° C. in 5 minutes. The pNP concentrations were calibrated based on spectrophotometric absorbance at OD$_{405}$. The cellobiase activities were assessed by cellobiose reducing rate and/or glucose producing rate where cellobiose and glucose concentrations were determined by HPLC (high performance liquid chromatography) analyses. Additionally, CMCase (for endo-glucanase activity), xylanase (for xylose hydrolyzing activity), avicelase (for exo-glucanase activity), and FPase (representing total cellulase activity) were measured based on production rate of reducing sugars that were detected by DNS (dinitrosalicyclic acid) method.

II. Results

Figure 3:
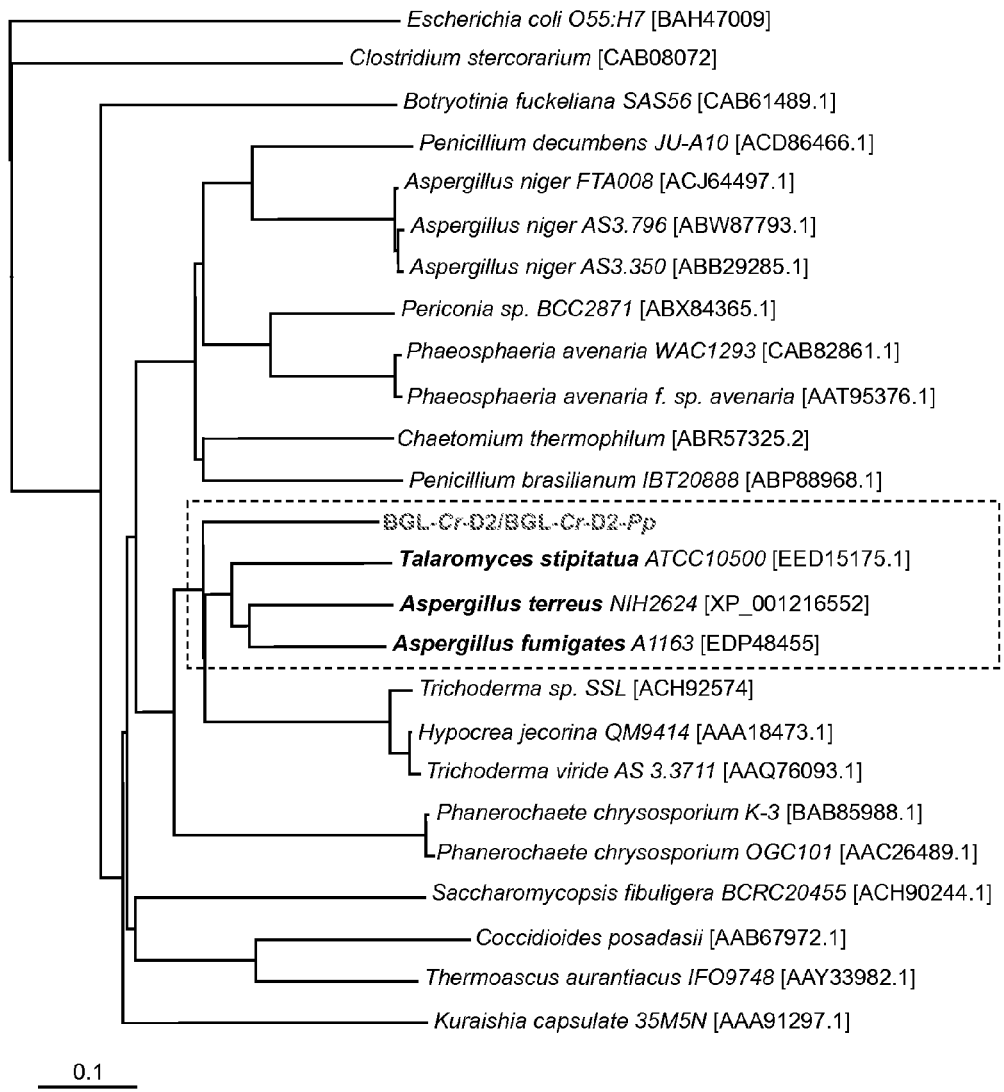
FIG. 3 is a diagram of the phylogenetic tree based on amino acid sequences of beta-glucosidase (BGL) from glycoside hydrolase (GH) family 3, showing that the BGL-Cr-D2-Pp secreted from reconstructed *Pichia pastoris* (strain SMD 1168) was related to the beta-D-glucoside glucohydrolase (i.e., BGL) of *T. stipitatua*, *A. terreus* NIH2624, and *A. fumigates* A1163 (i.e., 64-65% similarity in AA sequences).

In this invention, a Taiwan-indigenous fungus *Chaetomella raphigera* strain D2 was first found capable of secreting crude enzyme with significant β-glucosidase activity based on assessment using pNPG (p-nitrophenyl-β-D-glucopyranoside) and cellobiose as substrates. The gene (bgl-Cr-D2) encoding the target β-glucosidase (BGL-Cr-D2) was derived from genomic DNA and reverse-transcribed cDNA. It showed that the bgl-Cr-D2 cDNA had a size of 2166 bps (not including signal sequence and stop codon) and the bgl-Cr-D2 genomic DNA has a size of 2851 bps (FIGS. 1 & 2). Twelve introns were identified after comparing the bgl-Cr-D2 genomic DNA with cDNA. The bgl-Cr-D2 gene would encode 722 bases of amino acid to form the BGL-Cr-D2 (FIG. 2). Based on the comparison of the amino acid sequences for the β-glucosidases derived from glycoside hydrolase (GH) family 3, the newly-found BGL-Cr-D2 was homologous to the β-D-glucoside glucohydrolase of *Talaromyces stipitatua* (65% similarity) and *Aspergillus terreus* (64% similarity) (FIG. 3). Based on the phylogenetic analyses, *C. raphigena* D2, *T. stipitatua*, and *A. terreus* formed a sub-group that could distinguish from other fungal and bacterial groups (e.g., *Penicillium, Sacharomycopis, Clostridium*, and *Escherichia coli*).

Figure 4:
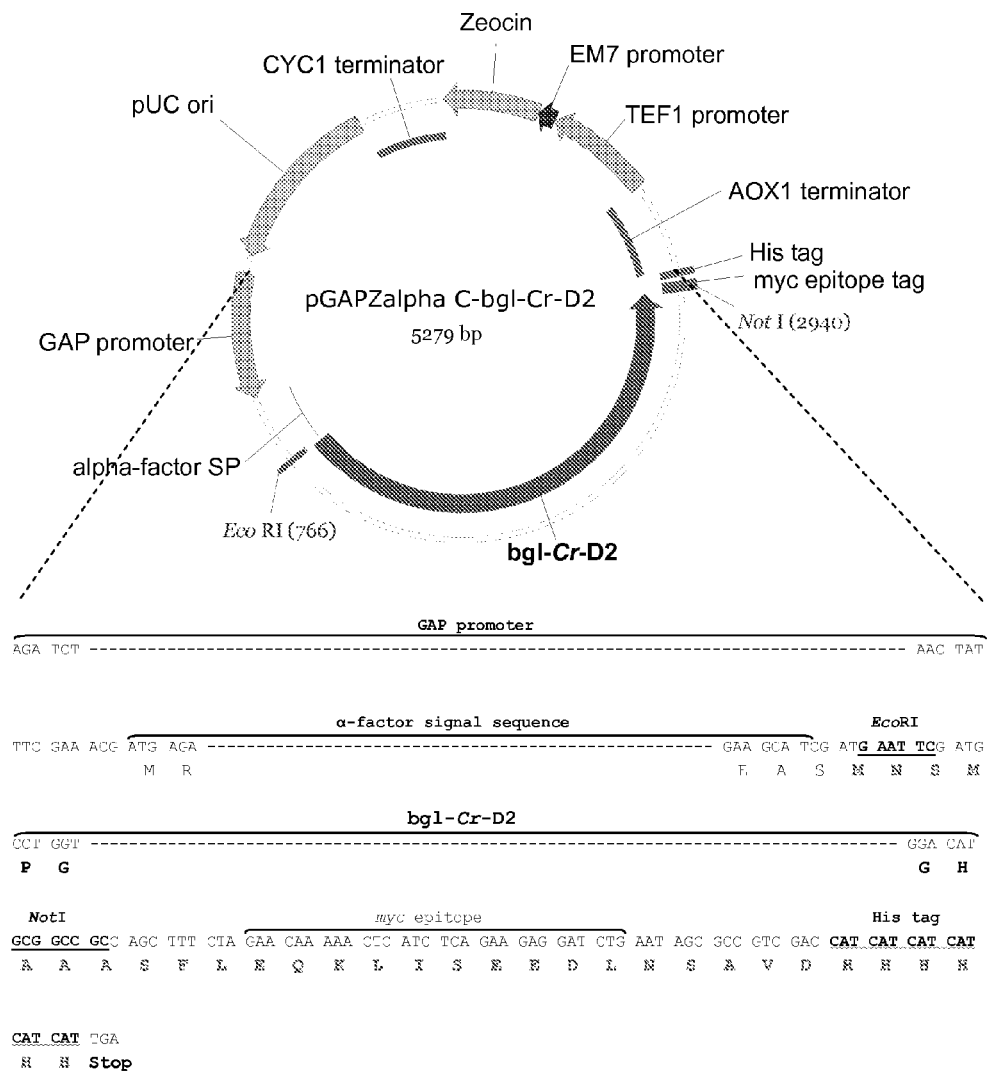
FIG. 4 is a diagram of a vector map of reconstructed pGAPZαC, showing that the bgl-Cr-D2 gene was cloned for further transformation to *P. pastoris* expression system. (In the simplified nucleotide sequence showed below the map, the lengths of shortened regions, i.e., GAP promoter, α-factor signal sequence, and bgl-Cr-D2, do not correlate to the real sizes as scaled in the diagram map.)
Figure 5:
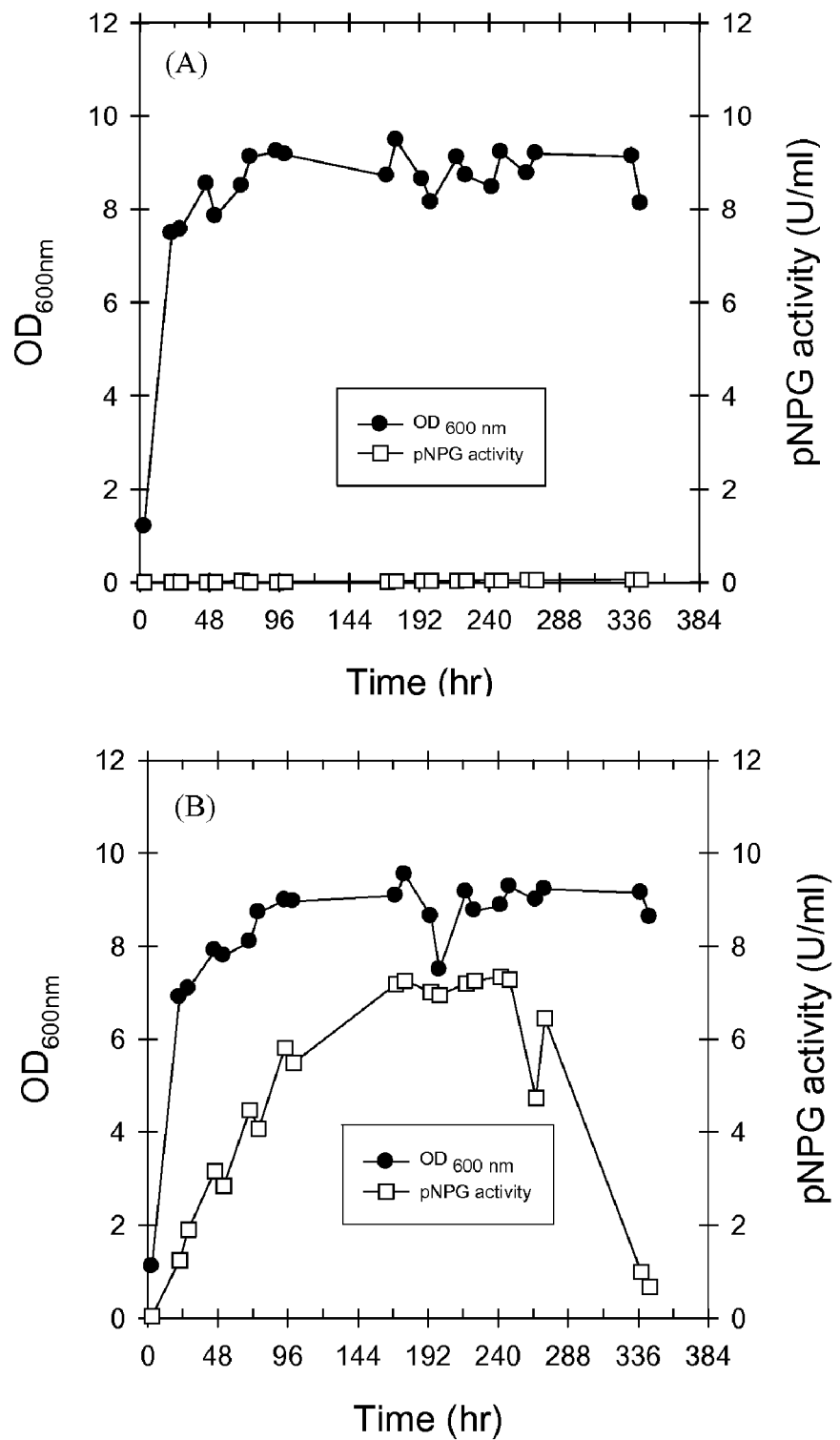
FIGS. 5A and 5B are diagrams showing growth and pNPGase activity versus time for the colonies of (A) *Pichia pastoris* strain SMD1168 and (B) *P. pastoris* strain SMD1168 carrying bgl-Cr-D2; they show similar growth profile but significant pNPGase activity only for the colony cloned with bgl-Cr-D2.
Figure 6:
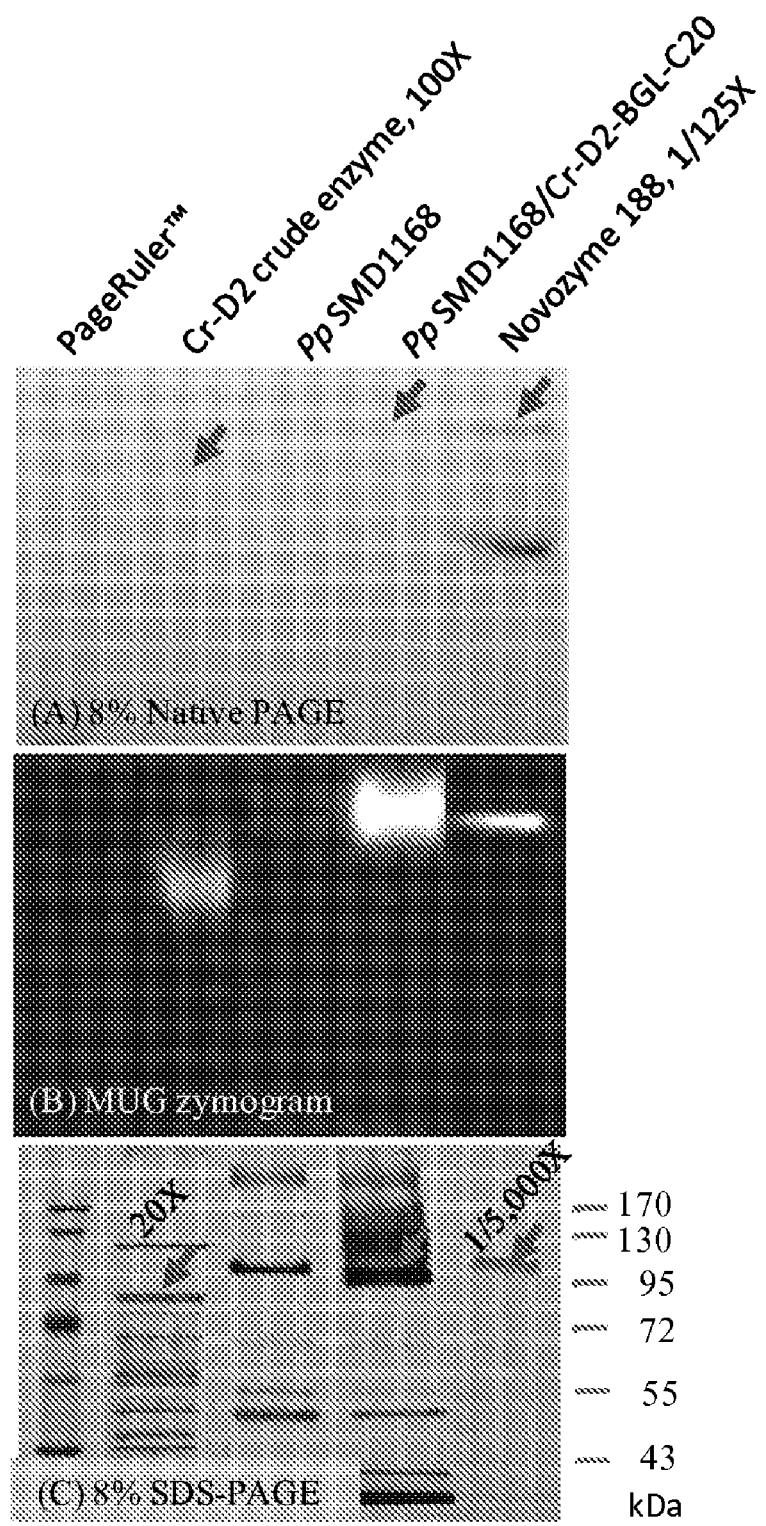
FIGS. 6A-C are photographs showing enzymes sizes and activities of native PAGE (A), MUG zymogram (B) and SDS PAGE (C). (Pp: *Pichia pastoris*; Cr-D2: *Chaetomella raphigera* fungus strain D2; BGL: beta-glucosidase).

The bgl-Cr-D2 gene was further cloned into pGAPZαC vector (FIG. 4) and transformed to a yeast expression system using *Pichia pastoris* strain SMD1168 as host cells. When compared the growth and pNPGase activity for the *Pichia pastoris* strain SMD1168 and that carrying bgl-Cr-D2, significant pNPGase activity was observed only for the colony cloned with bgl-Cr-D2 while the growth profiles were similar for the both colonies (FIG. 5). The growth and activity reached plateau levels after incubating at 30° C. for around 4-6 days. Furthermore, the recombinant β-glucosidase (BGL-Cr-D2-Pp) had a molecular size of around 95 kDa (FIG. 6C) (larger than theoretical size of 79 kDa due to post-translational glycosylation); and, showed high specific activity based on assessments of saccharifying rate (Table 1) and observations from native PAGE (polyacrylamide gel electrophoresis) (FIG. 6A)/MUG (4-methylumbelliferyl-β-D-glucopyranoside) zymogram (FIG. 6B).

Figure 7:
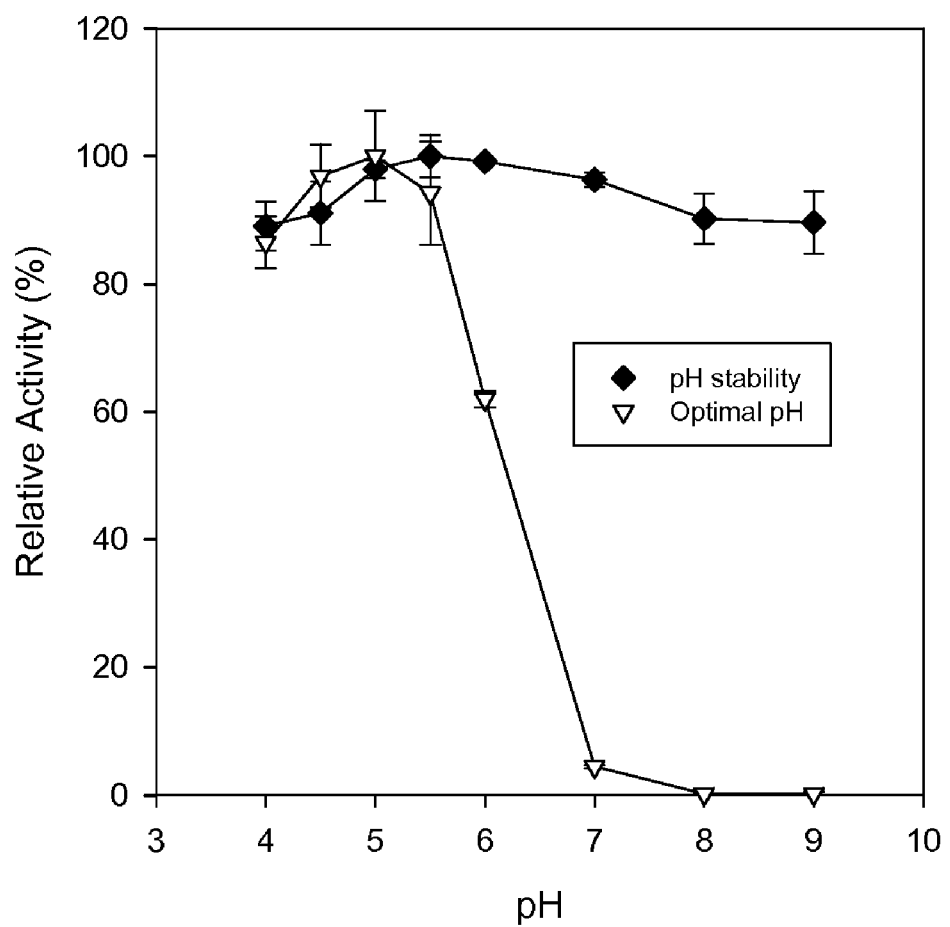
FIG. 7 is a diagram showing that the recombinant enzyme BGL-Cr-D2-Pp was stable over a wide pH range (4-9) based on 20-hour pH stability assessment (incubated the enzyme at 4° C. under each of the particular pH levels for 20 hours prior to performing standard pNPGase activity measurement, i.e., pH5 and 55° C. for 10 mins). The optimal pH level for pNPGase activity of the BGL-Cr-D2-Pp was around 5 (measured pNPGase activity of the enzyme at each of the particular pH levels).
Figure 8:
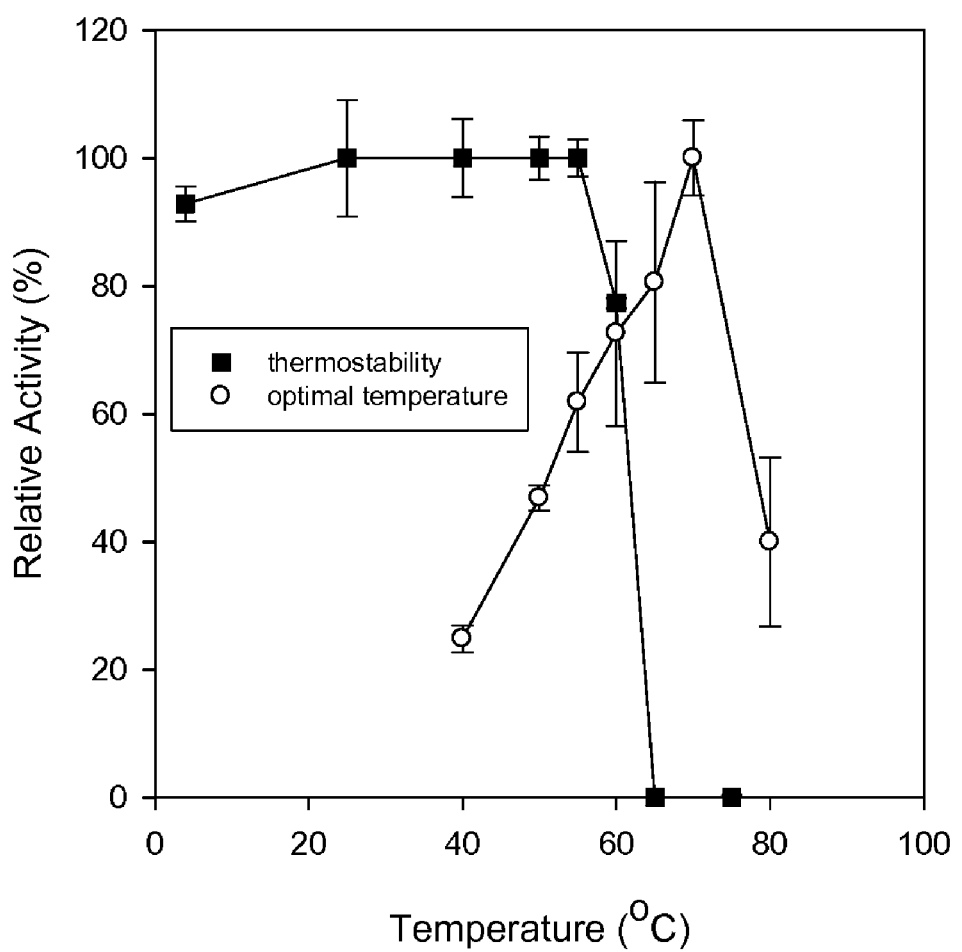
FIG. 8 is a diagram showing that the recombinant enzyme BGL-Cr-D2-Pp was stable under a temperature range of 4-55° C. based on 4-hour thermostability assessment (incubated the enzyme under each of the particular temperature for 4 hours prior to performing standard pNPGase activity measurement). Optimal temperature for pNPGase activity of the BGL-Cr-D2-Pp was around 70° C. (measured pNPGase activity of the enzyme at each of the particular temperature); but, at this high temperature, the enzyme would become inactive after longer incubation time (e.g., ≧2 hrs, FIG. 9).
Figure 9:
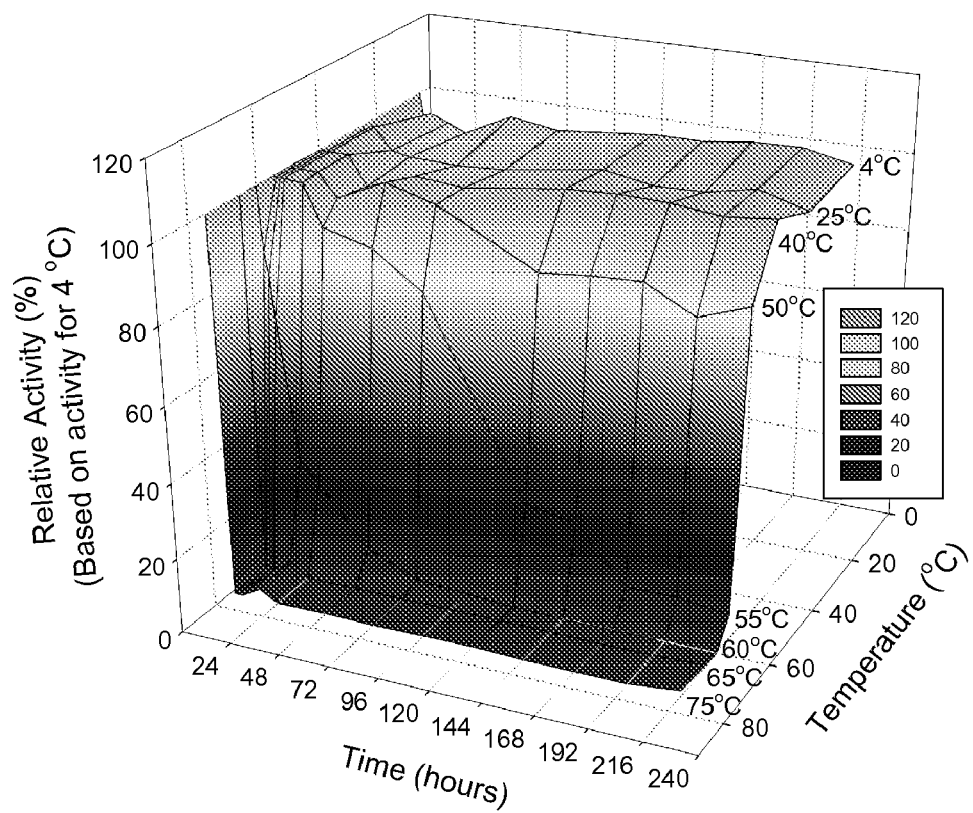
FIG. 9 is a 3-D diagram showing that thermostability of the recombinant β-glucosidase BGL-Cr-D2-Pp under temperature ranged from 4 to 75° C. over a 9-days period. Under a temperature ≦50° C., the BGL-Cr-D2-Pp remained stable (relative activity >80%) over 9 days.

The recombinant BGL-Cr-D2-Pp remained active after 20-hour incubation under a wide pH range (i.e., pH4-pH9) (FIG. 7). However, the pNPGase activity of this enzyme significantly decreased at pH levels higher than 5.5. Besides, the BGL-Cr-D2-Pp had highest pNPGase activity at a temperature of 75° C.; but, at this high temperature, the activity dropped tremendously after short-term incubation (i.e., 2 hours) (FIGS. 8 & 9). Thus, the pNPGase activities of the recombinant BGL-Cr-D2-Pp were performed at pH 5 and a temperature of 55° C. for 10 minutes.

TABLE 1

Comparison of enzyme activities for native BGL-Cr-D2, *Pichia pastoris* strain SMD1168 secretes, recombinant BGL-Cr-D2-Pp secreted from *P. pastoris*, and Novozyme-188 for different substrates (all reactions were performed at pH 5 and 55° C).

| Substrates | Reaction time (minutes) | Activity (U**/mg BGL) | | | |
|---|---|---|---|---|---|
| | | BGL-Cr-D2 | Pp SMD1168 | BGL-Cr-D2-Pp | N-188 |
| 2 mM pNPG* | 5 | 1,029.9 | 41.1 | 2,963.9 | 171.7 |
| 2 mM Cellobiose | 5 | — | — | 57.5 | 11.1 |

| Substrates | Reaction time (minutes) | Activity (U/mg enzymes††) | | | |
|---|---|---|---|---|---|
| | | BGL-Cr-D2 | Pp SMD1168 | BGL-Cr-D2-Pp | N-188 |
| 1% CMC† | 30 | 121.1 | 1.0 | 0.7 | 1.1 |
| 1% Xylan | 30 | 186.9 | 0.0 | 3.8 | 3.4 |

TABLE 1-continued

Comparison of enzyme activities for native BGL-Cr-D2, Pichia pastoris strain SMD1168 secretes, recombinant BGL-Cr-D2-Pp secreted from P. pastoris, and Novozyme-188 for different substrates (all reactions were performed at pH 5 and 55° C).

| 1% Avicel | 120 | 0.0 | 0.2 | 0.0 | 0.0 |
| FP‡ | 120 | 0.1 | 0.0 | 0.1 | 0.0 |

*p-nitrophenyl-β-D-glucopyranoside; †carboxymethylcellulose; ‡filter paper; **1 U = 1 μmole pNP produced from pNPG, glucose produced from cellobiose, or reduced saccharides produced from CMC, xylan, avicel or FP per minute; ††total enzymes except BGL.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated polypeptide comprising a sequence at least 90% identical to SEQ ID NO: 1, wherein the polypeptide has a β-glucosidase activity.

2. The isolated polypeptide of claim 1, wherein the sequence is at least 95% identical to SEQ ID NO: 1.

3. The isolated polypeptide of claim 2, wherein the sequence is at least 99% identical to SEQ ID NO: 1.

4. The isolated polypeptide of claim 3, wherein the polypeptide includes the sequence of SEQ ID NO: 1.

5. An isolated nucleic acid encoding the polypeptide of claim 1.

6. The nucleic acid of claim 5, wherein the nucleic acid comprises the sequence of SEQ ID NO: 2, 3, 5, or 6.

7. An expression vector comprising a nucleic acid of claim 5.

8. A host cell comprising a nucleic acid of claim 5.

9. A method of producing a polypeptide, comprising
culturing in a medium a host cell that contains a nucleic acid encoding the polypeptide of claim 1 under conditions permitting expression of the polypeptide encoded by the nucleic acid, and
purifying the polypeptide from the cultured cell or the medium of the cell.

10. The method of claim 9, wherein the polypeptide has a sequence that is 90% identical to SEQ ID NO: 1.

11. The method of claim 9, wherein the polypeptide has a sequence that is 95% identical to SEQ ID NO: 1.

12. The method of claim 9, wherein the polypeptide has the sequence of SEQ ID NO: 1.

13. A composition comprising a polypeptide of claim 1.

14. The composition of claim 13, wherein the composition further comprises an exoglucanase and an endoglucanase.

15. A method of producing fermentable sugars from lignocellulosic material, comprising
providing a composition of claim 13, and
contacting the composition with lignocellulosic material to produce fermentable sugars.

16. The method of claim 15, wherein the fermentable sugar is elected from the group consisting of glucose, xylose, arabinose, galactose, mannose, rhamnose, sucrose, fructose, lactose, maltose, trehalose, and cellobiose.

17. The method of claim 15, wherein the polypeptide has the amino acid sequence of SEQ ID NO:1.

18. The method of claim 15, wherein the lignocellulosic material is selected from the group consisting of cellulosic animal waste, municipal solid waste, waste paper, yard waste, an agricultural residue, and a forestry residue.

19. The method of claim 15, further comprising converting the fermentable sugar to a fermentation product.

20. The method of claim 19, wherein the converting step is performed by microorganism fermentation or enzyme treatment.

21. A method of producing energy from lignocellulosic material, comprising provinding a composition of claim 13;

contacting the composition with the lignocellulosic material to produce a fermentable sugar;

converting the fermentable sugar to produce a combustible fermentation product, and combusting the combustible fermentation product to produce energy.

* * * * *